United States Patent
Fu et al.

(10) Patent No.: US 11,873,321 B2
(45) Date of Patent: Jan. 16, 2024

(54) COMPOSITIONS AND METHODS FOR TREATING ALZHEIMER'S DISEASE

(71) Applicant: Generos Biopharma Ltd., Shanghai (CN)

(72) Inventors: Xin-Yuan Fu, Moreno Valley, CA (US); Yi Zhou, Singapore (SG)

(73) Assignee: GenEros Biopharma Ltd., Shanghai (CN)

( * ) Notice: Subject to any disclaimer, the term of this patent is extended or adjusted under 35 U.S.C. 154(b) by 4 days.

(21) Appl. No.: 16/613,264

(22) PCT Filed: May 9, 2018

(86) PCT No.: PCT/US2018/031901
§ 371 (c)(1),
(2) Date: Nov. 13, 2019

(87) PCT Pub. No.: WO2018/213081
PCT Pub. Date: Nov. 22, 2018

(65) Prior Publication Data
US 2020/0199239 A1 Jun. 25, 2020

Related U.S. Application Data

(60) Provisional application No. 62/506,782, filed on May 16, 2017.

(51) Int. Cl.
| | | |
|---|---|---|
| *A61P 25/28* | (2006.01) | |
| *A61K 31/7105* | (2006.01) | |
| *C12N 9/22* | (2006.01) | |
| *C07K 16/28* | (2006.01) | |
| *A61K 31/366* | (2006.01) | |
| *A61K 31/575* | (2006.01) | |
| *C07K 16/24* | (2006.01) | |

(52) U.S. Cl.
CPC ........ *C07K 16/2866* (2013.01); *A61K 31/366* (2013.01); *A61K 31/575* (2013.01); *A61K 31/7105* (2013.01); *A61P 25/28* (2018.01); *C07K 16/248* (2013.01); *C07K 16/249* (2013.01); *C12N 9/22* (2013.01)

(58) Field of Classification Search
CPC ............... A61K 31/366; A61K 31/575; A61K 31/7105; C07K 16/2866; C07K 14/4705; A61P 25/28; C12N 9/22; C12N 15/00; C12Y 114/99038
See application file for complete search history.

(56) References Cited

U.S. PATENT DOCUMENTS

| | | | | |
|---|---|---|---|---|
| 2002/0188012 A1* | 12/2002 | Bisgaier | ............... | A61K 31/195 514/356 |
| 2003/0138404 A1* | 7/2003 | Maroun | ............. | A61K 38/1793 424/85.5 |
| 2006/0275294 A1 | 12/2006 | Omoigui | | |
| 2016/0145646 A1* | 5/2016 | Frendewey | .......... | C12Q 1/6888 800/24 |
| 2017/0100329 A1* | 4/2017 | Kovarik | ............... | A61K 35/741 |

FOREIGN PATENT DOCUMENTS

WO WO-2015/168800 A1 11/2015

OTHER PUBLICATIONS

Van Cauwenberghe et al. The genetic landscape of Alzheimer disease: clinical implications and perspectives. Genet Med 18, 421-430 (2016).*
Lee et al. Simvastatin inhibits IFN-gamma-induced CD40 gene expression by suppressing STAT-1alpha. J Leukoc Biol. Aug. 2007;82(2):436-47. doi: 10.1189/jlb.1206739. Epub May 16, 2007.*
Lathe et al. Atherosclerosis and Alzheimer—diseases with a common cause? Inflammation, oxysterols, vasculature. BMC Geriatr 14, 36 (2014). https://doi.org/10.1186/1471-2318-14-36.*
Extended European Search Report dated Mar. 31, 2021 issued in European Patent Application No. 18802949.0, 9 pages.
Minogue, Aedin M., et al., "LPS-induced release of IL-6 from glia modulates production of IL-1β in a JAK2-dependent manner," Journal of Neuroinflammation, 2012,9:126, 10 pages, doi: 10.1186/1742-2094-9-126.
Zhang, Yuan-Yuan, et al., "Atorvastatin attenuates the production of IL-Iβ, IL-6, and TNF-α in the hippocampus of an amyloid β1-42-induced rat model of Alzheimer's disease," Clinical Interventions in Aging, 2013, vol. 8, pp. 103-110.
International Preliminary Report on Patentability issued in corresponding PCT Application No. PCT/US2018/031901 dated Nov. 28, 2019.
Balschun, D., et al., "Interleukin-6: a cytokine to forget," The FASEB Journal, 2004, vol. 18, No. 14, pp. 1788-1790, doi: 10.1096.fj.04-1625fje.
Browne, Tara C., et al., "IFN-γ Production by Amyloid β-Specific Th1 Cells Promotes Microglial Activation and Increases Plaque Burden in a Mouse Model of Alzheimer's Disease," The Journal of Immunology, 2013, vol. 190, pp. 2241-2251, doi: 10.4049/jimmunol.org/content/190/5/2241.
Fassbender, K., et al., "Simvastatin strongly reduces levels of Alzheimer's disease β-amyloid peptides Aβ42 and Aβ40 in vitro and in vivo," Proceedings of the National Academy of Sciences of the United States of America, 2001, vol. 98, No. 10, pp. 5856-5861, www.pnas.org/cgi/doi/10.1073/pnas.081620098.
Hsu, Wei-Lun, et al., "STAT1 Negatively Regulates Spatial Memory Formation and Mediates the Memory-Impairing Effect of Aβ," Neuropsychopharmacology, 2014, vol. 39, pp. 746-758.

(Continued)

*Primary Examiner* — Kimberly Ballard
*Assistant Examiner* — Stacey N MacFarlane
(74) *Attorney, Agent, or Firm* — FOLEY & LARDNER LLP

(57) ABSTRACT

Disclosed are methods for treating or preventing or delaying outset of Alzheimer's disease (AD) in a subject by targeting the novel pathway STAT1-CH25H in AD pathogenesis, specifically by administering to the subject a pharmaceutically effective amount of a STAT1 inhibitor, a CH25H inhibitor, or a 25-OHC inhibitor, for example, a 3-hydroxy-3-methyl-glutaryl-coenzyme A (HMG-CoA) reductase inhibitor such as simvastatin.

6 Claims, 57 Drawing Sheets
Specification includes a Sequence Listing.

(56) References Cited

OTHER PUBLICATIONS

Jin, Peng, et al., "Anti-inflammatory and anti-amyloidogenic effects of a small molecule, 2,4-bis(p-hydroxyphenyl)-2-butenal in Tg2576 Alzheimer's disease mice model," Journal of Neuroinflammation, 2013, vol. 10, Issue 2, doi: 10.1186/1742-2094-10-2.

Matsumiya, Tomoh, et al., "How are STAT1 and cholesterol metabolism associated in antiviral responses?", JAK-STAT 2013, 2:e24189, http://dx.doi.org/10.4161/jkst.24189, 4 pages.

Murlidharan, Giridhar, et al., "CNS-restricted Transduction and CRISPR/Cas9-mediated Gene Deletion with an Engineered AAV Vector," Molecular Therapy-Nucleic Acids, Official journal of the American Society of Gene & Cell Therapy, 2016, vol. 5, No. 7, e338, doi: 10.1038/mtna.2016.49, 12 pages.

Wu, Ya-Ying, et al., "Alterations of the Neuroinflammatory Markers IL-6 and TRAIL in Alzheimer's Disease," Dementia and Geriatric Cognitive Disorders Extra, 2015, vol. 5, No. 3, pp. 424-434, doi: 10.1159/000439214.

Zhang, Yuan-Yuan, et al., "Atorvastatin attenuates the production of IL-Iβ, IL-6, and TNF-α in the hippocampus of an amyloid βI-42-induced rat model of Alzheimer's disease," Clinical Interventions in Aging, 2013, vol. 8, p. 103-110, doi: 10.2147/CIA.S40405.

Decision of Final Rejection dated May 10, 2022 issued in JP Application No. 2019-563786, with English translation, 11 pages.

Communication pursuant to Article 94(3) EPC dated May 9, 2023 issued in EP Application No. 18 802 949.0, 5 pages.

Decision of the Intellectual Property Office dated Feb. 21, 2023 issued in TW Application No. 107116606, with English translation, 15 pages.

Notice of Preliminary Rejection dated Mar. 9, 2023 issued in KR Application No. 10-2019-7036561, with English translation, 17 pages.

Notice of Final Rejection dated Aug. 23, 2023 issued in KR Application No. 10-2019-7036561, with English translation, 9 pages.

Notice of Reasons for Rejection dated Aug. 1, 2023 issued in JP Application No. 2022-143550, with English translation, 18 pages.

Amano, Koichi, Basic course for clinical rheumatologists, Janus Kinases and rheumatic diseases, Clin Rheumatol, 2014, vol. 26, No. 4, p. 330 332, doi:10.14961/cra.26.330 (partial English translation).

Devaux, Patricia, et al., "The measles virus phosphoprotein interacts with the linker domain of STAT1", Virology, 2013, vol. 444, No. 1-2, p. 250-256, doi:10.1016/j.virol.2013.06.019.

Elcioglu, H. Kubra, et al., "Tocilizumab's effect on cognitive deficits induced by intracerebroventricular administration of streptozotocin in Alzheimer's model," Mol Cell Biochem, 2016, vol. 420, pp. 21-28, DOI 10.1007/s11010-016-2762-6.

Examination Report No. 1 dated Feb. 15, 2023 issued in AU Application No. 2018270906, 5 pages.

Office Action dated Nov. 22, 2022 issued in JP Application No. 2019-563786, with English translation, 17 pages.

Ono, Kenjiro, et al., "Aβ aggregation mechanism and its regulation", Journal of Clinical and Experimental Medicine (Igaku No Ayumi), 2009, vol. 229, No. 5, pp. 405-408. (partial English translation).

Papassotiropoulos, Andreas, et al., "Cholesterol 25-Hydroxylase on Chromosome 10q is a Susceptibility Gene for Sporadic Alzheimer's Disease", Neurodegenerative Diseases, 2005, vol. 2, No. 5, p. 233-241, doi: 10.1159/000090362.

Park, Wungki, et al., "New perspectives of curcumin in cancer prevention", Cancer Prevention Research, 2013, vol. 6, No. 5, pp. 387-400, doi: 10.1158/1940-6207.CAPR-12-0410.

Peng, Li, et al., "Molecular basis for antagonistic activity of anifrolumab, an anti-interferon-a receptor 1 antibody," mAbs, Mar./Apr. 2015, vol. 7, No. 2, pp. 428-439.

Taylor, Juliet M., et al., "Type-1 interferon signaling mediates neuro-inflammatory events in models of Alzheimer's disease," Neurobiology of Aging, 2014, vol. 35, No. 5, pp. 1012-1023, DOI:10.1016/j.neurobiolaging.2013.10.089.

First Office Action dated Feb. 24, 2023 issued in CN Application No. 201880045403.4, with English translation, 11 pages.

* cited by examiner

25-OHC

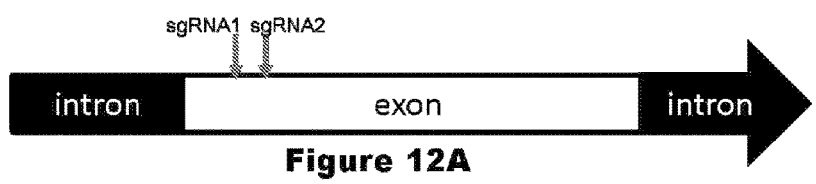
Figure 12A
| mouse Ch25h sgRNA1 | GGCAGAAGCTGCTTTACGGA |
| mouse Ch25h sgRNA2 | GCTGACACTCTACCAGCACC |
Figure 12B
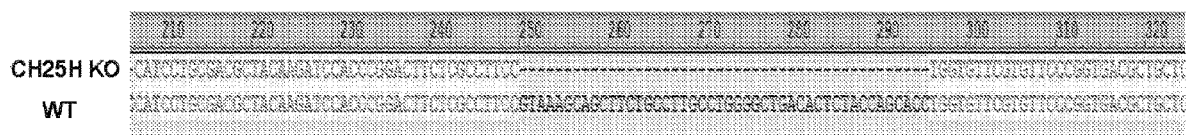
Figure 12C

APP/PS1  APP/PS1/STAT1−/−

COMPOSITIONS AND METHODS FOR TREATING ALZHEIMER'S DISEASE

SEQUENCE LISTING

The instant application contains a Sequence Listing which has been filed electronically in ASCII format and is hereby incorporated by reference in its entirety. Said ASCII copy, created on Nov. 25, 2019, is named 119617-0131_SL.txt and is 799 bytes in size.

FIELD OF INVENTION

This invention relates generally to the field of pharmaceutical agents and uses of the pharmaceutical agents for disease treatments thereof, specifically the pharmaceutical agents that target and inhibit the signal transducer and activator of transcription 1 (STAT1), the Cholesterol 25-Hydroxylase (CH25H), and 25-hydroxylated cholesterol (25-OHC); and uses of the pharmaceutical agents in managing physiological conditions, specially the treatment and/or prevention of various diseases including central nervous system disorders, neurodegenerative diseases such as Alzheimer's disease and other diseases by reducing amyloid beta depositions.

BACKGROUND

With the increasing life span of our population, Alzheimer's disease (AD) is becoming a prevalent health problem worldwide. AD patient suffer from cognitive decline in their memory, orientation, judgment, and reasoning (Tanzi and Bertram 2005). Typically, the disease development takes about 10 years to the final stage that leads to death. Up to now, no cure or preventative therapy is available.

The deposition of A$\beta$ protein, which is a metabolite of amyloid precursor protein (hereinafter referred to as APP), along with their toxicity in the brain, is considered to be the primary causal factor for the development of AD (Selkoe 2001). A$\beta$ is the protein component identified in the senile plaques found in AD patients (Ikeda, Wong et al. 1987, Cole, Masliah et al. 1991). Biologically, A$\beta$ is generated through sequential cleavage of Amyloid-$\beta$ Precursor Protein (APP), which yields fragments of different size. Pharmaceutical studies have identified A$\beta$42 as the most pathogenic form contributing to the development of AD (Roher, Chaney et al. 1996, Morelli, Prat et al. 1999). Production of A$\beta$42 is a result from $\beta$- and subsequent $\gamma$-cleavage of APP (Citron 2010, De Strooper, Vassar et al. 2010). This insoluble A$\beta$42 fragment aggregates in the extracellular space to form plaques. Several lines of evidence suggest the soluble oligomers of A$\beta$42 are even more toxic. The presence of A$\beta$42 has an impact on synaptic activities. Accumulation of A$\beta$42 could potentially induce aberrant network activity and synaptic depression (Palop and Mucke 2009).

Preclinical studies in transgenic mouse models have shown immunotherapy has great efficacy in the prevention of both AD and prion diseases (Wisniewski 2012). Knowing A$\beta$ is the central molecule in AD, several strategies have been developed towards the eradication of A$\beta$ via small molecules or immunotherapies (Tabira 2011, Huang and Mucke 2012, Ozudogru and Lippa 2012, Delrieu, Ousset et al. 2014). Although A$\beta$-directed immunization had promising results in mouse models of AD, the translation to effective therapy for humans is still challenging.

In the active vaccination trials, individuals having received active immunization showed a significant decrease in plaque burden and strikingly reduced A$\beta$ relative to non-immunized controls. Regardless of the encouraging results, the treatment group showed no improvements in long-term survival, time to develop severe dementia, and cognitive functions (Holmes, Boche et al. 2008). Two recent, large phase III trials of passive immunization targeting A$\beta$ also have ended up with no evidence of clinical benefits (Doody, Thomas et al. 2014, Salloway, Sperling et al. 2014). Therefore, it is desirable to find new and novel treatments or preventive theapies for AD.

BRIEF SUMMARY OF THE INVENTION

In one aspect, the present invention is a method of treating Alzheimer's disease (AD) in a subject by administering to the subject a pharmaceutically effective amount of a STAT1 inhibitor. In one embodiment, the STAT1 inhibitor is an antibody against IFN or IFN receptor. In another embodiment, the STAT1 inhibitor is an antibody against IL-6 or IL6 receptor. In still another embodiment, the STAT1 inhibitor is an agent that inhibits JAK1 and JAK3. In yet still another embodiment, the STAT1 inhibitor is an agent that reduces STAT1 phosphorylation. In a further embodiment, the STAT1 inhibitor is an agent that prevents the translocation of STAT1 into nucleus. In a further embodiment, the STAT1 inhibitor is an RNAi agent against STAT1.

In another aspect, the present invention is a method of treating Alzheimer's disease (AD) in a subject by administering to the subject a pharmaceutically effective amount of a CH25H inhibitor. In some embodiments, the CH25H inhibitor is a STAT1 inhibitor. In another embodiment, the CH25H inhibitor is a STAT1 inhibitor that is an antibody against IFN or IFN receptor. In yet another embodiment, the CH25H inhibitor is a STAT1 inhibitor that is an antibody against IL-6 or IL6 receptor. In still another embodiment, the CH25H inhibitor is a STAT1 inhibitor that is an agent that inhibits JAK1 and JAK3. In a further embodiment, the CH25H inhibitor is a STAT1 inhibitor that is an agent that reduces STAT1 phosphorylation. In a further embodiment, the CH25H inhibitor is a STAT1 inhibitor that is an agent that prevents the translocation of STAT1 into nucleus. In still a further embodiment, the CH25H inhibitor is a STAT1 inhibitor that is an RNAi agent against STAT1.

In another aspect, the present invention is a method of treating Alzheimer's disease (AD) in a subject by administering to the subject a pharmaceutically effective amount of a 25-OHC inhibitor. In one embodiment, the 25-OHC inhibitor is an CH25H inhibitor or a STAT1 inhibitor. In another embodiment, the 25-OHC inhibitor is an analog of 25-OHC. In yet another embodiment, the 25-OHC inhibitor is a 3-hydroxy-3-methyl-glutaryl-coenzyme A (HMG-CoA) reductase inhibitor, for example, simvastatin.

In another aspect, the present invention is a method of preventing or delaying onset of Alzheimer's disease (AD) in a subject by administering to the subject a pharmaceutically effective amount of a STAT1 inhibitor. In one embodiment, the STAT1 inhibitor is an antibody against IFN or IFN receptor. In another embodiment, the STAT1 inhibitor is an antibody against IL-6 or IL-6 receptor. In yet another embodiment, the STAT1 inhibitor is an agent that inhibits JAK1 and JAK3. In still another embodiment, the STAT1 inhibitor is an agent that reduces STAT1 phosphorylation. In a further embodiment, the STAT1 inhibitor is an agent that prevents the translocation of STAT1 into nucleus. In still a further embodiment, the STAT1 inhibitor is an RNAi agent against STAT1.

In yet another aspect, the present invention is a method of preventing or delaying onset of Alzheimer's disease (AD) in a subject by administering to the subject a pharmaceutically effective amount of a CH25H inhibitor. In some embodiments, the CH25H inhibitor is a STAT1 inhibitor. In one embodiment, the STAT1 inhibitor is an antibody against IFN or IFN receptor. In another embodiment, the STAT1 inhibitor is an antibody against IL-6 or IL-6 receptor. In yet another embodiment, the STAT1 inhibitor is an agent that inhibits JAK1 and JAK3. In still another embodiment, the STAT1 inhibitor is an agent that reduces STAT1 phosphorylation. In a further embodiment, the STAT1 inhibitor is an agent that prevents the translocation of STAT1 into nucleus. In still a further embodiment, the STAT1 inhibitor is an RNAi agent against STAT1.

In still another aspect, the present invention is a method of preventing or delaying onset of Alzheimer's disease (AD) in a subject by administering to the subject a pharmaceutically effective amount of a 25-OHC inhibitor. In some embodiments, the 25-OHC inhibitor is an CH25H inhibitor or a STAT1 inhibitor. In other embodiments, the 25-OHC inhibitor is an analog of 25-OHC. In still other embodiments, the 25-OHC inhibitor is a 3-hydroxy-3-methyl-glutaryl-coenzyme A (HMG-CoA) reductase inhibitor, for example, simvastatin.

In still another embodiments, the present invention is a method of treating Alzheimer's disease (AD) in a subject by providing a genome editing tool; delivering the genome editing tool to neural cells; and editing the STAT1 gene by deleting the entire STAT1 gene, the phosphrylation site of the STAT1 gene, the promoter region of the STAT1 gene, or the SH2 domain of the STAT1 gene. In some embodiments, the genome editing tool is a CRISPR-CAS9 system.

In still another aspect, the present invention is a method of treating Alzheimer's disease (AD) in a subject by providing a genome editing tool; delivering the genome editing tool to neural cells; and editing the CH25H gene by deleting the entire CH25H gene, the histine cluster regions of the CH25H gene, or the promoter region of the CH25H gene. In some embodiments, the genome editing tool is a CRISPR-CAS9 system.

In a further aspect, the present invention is a method of preventing or delaying onset of Alzheimer's disease (AD) in a subject by providing a genome editing tool; delivering the genome editing tool to neural cells; and editing the STAT1 gene by deleting the entire STAT1 gene, the phosphrylation site of the STAT1 gene, the promoter region of the STAT1 gene, or the SH2 domain of the STAT1 gene. In some embodiments, the genome editing tool is a CRISPR-CAS9 system.

In still a further aspect, the present invention is a method of preventing or delaying onset of Alzheimer's disease (AD) in a subject by providing a genome editing tool; delivering the genome editing tool to neural cells; and editing the CH25H gene by deleting the entire CH25H gene, the histine cluster regions of the CH25H gene, or the promoter region of the CH25H gene. In some embodiments, the genome editing tool is a CRISPR-CAS9 system.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A shows four images showing the staining of phosphorylated STAT1 (pSTAT1) in brain tissue from three AD patients (Case-1, Case-2 and Case-3) and a healthy person (Control). FIG. 1B shows an enlarged image to illustrate the morphology of pSTAT1 staining, which morphology suggest the accumulation of pSTAT1 within nuclei. See the staining within rectangular frames.

FIG. 2A shows images of staining of amyloid-beta (Aβ) in mouse model of AD (APP/PS1 mice) and AD mouse with STAT1 deficiency (APP/PS/STAT1−/−). Brain sections were obtained from 3-month-old of APP/PS1 and APP/PS1/STAT1−/− mice respectively. Images show the staining of Aβ in whole brain section as well as hippocampal area at higher magnification. FIG. 2B shows a graph depicting Aβ plaque number in 5 successive sections that were obtained from 3-month-old of APP/PS1 and APP/PS1/STAT1−/− mice respectively. FIG. 2C shows a graph depicting Aβ plaque area in 5 successive sections that were obtained from 3-month-old of APP/PS1 and APP/PS1/STAT1−/− mice respectively. FIG. 2D shows a graph depicting the Elisa measurement of Aβ42 in TBS extract of brain tissues that were obtained from 3-month-old of wildtype, APP/PS1 and APP/PS1/STAT1−/− mice respectively. FIG. 2E shows a graph depicting the Elisa measurement of Aβ42 in formic acid extract of brain tissues that were obtained from 3-month-old of wildtype, APP/PS1 and APP/PS1/STAT1−/− mice respectively. * means P value less than 0.05.

FIG. 3A shows a heatmap depicting the gene ontology analysis of differentially expressed genes with fold change >1.5, p value<0.05, two biological repeats used for each genotype. FIG. 3B shows a pie map depicting the pathway analysis of differentially expressed genes by David functional annotation clustering.

FIG. 4A shows a graph depicting results of real-time PCR quantification of CH25H mRNA level in brains of APP/PS1 and APP/PS1/STAT1−/− mice. Data is representative of 3 independent experiments. FIG. 4B shows images depicting results of Western blot of CH25H, STAT1 and α-tubulin in brain homogenate of 3 pairs of APP/PS1 and APP/PS1/STAT1−/− mice.

FIG. 5A shows a schematic representation of the CH25H gene and its promoter. FIG. 5B shows a graph depicting results of chromatin histone immune-precipitation (ChIP) experiment where DNA fragment containing CH25H promoter were enriched by STAT1 antibody pull down and this enrichment was diminished in sample from STAT1 KO (STAT1−/−) mice compared to that in wildtype (WT) mice.

FIG. 6A shows a graph depicting the results of measurement of total brain cholesterol level in APP/PS1 and APP/PS1/STAT1−/− mice. n=3 for each group. FIG. 6B shows a graph depicting results of measurement of 25-OHC level in same mice used for cholesterol measurement in FIG. 6A.

FIG. 8A shows images depicting results of Western blot with APP from samples made by collecting the medium for exosome purification and lysing the purified exosomes. FIG. 8B shows images depicting results of Western blot with APP from samples made by collecting cell lysate to assess intracellular APP level. FIG. 8C shows a graph depicting results of FACS analysis of surface APP in control and 25-OHC treated cells.

FIG. 10A shows images depicting the trafficking of APP molecules traced by FITC-conjugated antibody labelled surface APP. Cells were fixed at different time points to check the distribution of APP at specific time. FIG. 10B shows an image of a snapshot of a time-lapse video showing APP translocation overtime in control cells. FIG. 10C shows an image of a snapshot of a time-lapse video showing APP translocation in 25-OHC treated cells.

FIG. 11A shows images of brain tissue sections stated for amyloid-beta. Mice at 2-month-old were injected with 25-OHC or saline as control every other day for duration of 1 month. Brains from these mice were sectioned and stained for amyloid-beta. Data are representative of 3 pairs of saline or 25-OHC injected mice. FIGS. 11B and 11C show graphs depicting Aβ plaque number in 5 successive sections of whole brain (FIG. 11B) and Hippocampus (FIG. 11C) that were obtained from the Saline control and 25-OHC mice, respectively.

FIGS. 12A-12E show graphs and images depicting the generation of CH25H KO mice. FIG. 12A is a schematic view of CH25H gene and two targeting sgRNA. FIG. 12B shows the DNA sequence of two targeting sgRNA. FIG. 12C depicts the sequencing results showing deletion of CH25H gene in the CH25H knock out mice. FIG. 12D shows an image depicting the genotyping result of WT (534 bp) and KO (488 bp) bands, respectively. FIG. 12E shows a graph depicting the real-time PCR result of CH25H RNA level in WT and CH25H KO mice, respectively.

FIG. 13A are images showing the staining of amyloid-beta in mouse model of AD (APP/PS1 mice) and AD mouse with CH25H deficiency (APP/PS/CH25H−/−). Brain sections were obtained from 3-month-old of APP/PS1 and APP/PS1/CH25H−/− mice, respectively. Images show the staining of amyloid-beta in whole brain section as well as hippocampal area at higher magnification. FIGS. 13B and 13C show graphs depicting Aβ plaque number in 5 successive sections of whole brain (FIG. 13B) and Hippocampus (FIG. 13C) that were obtained from 3-month-old of APP/PS1 and APP/PS1/CH25H−/− mice, respectively.

FIG. 16A shows a graph depicting the results of real-time PCR quantification of APP mRNA level in brains of APP/PS1 and APP/PS1/STAT1−/− mice. FIGS. 16B, 16C and 16D show three graphs depicting results of real-time PCR quantification of Adam10 (FIG. 16B), BACE1 (FIG. 16C) and Nicastrin (FIG. 16D), i.e., the α, β, and γ secretase of APP, respectively. Data is representative of 3 independent experiments.

FIGS. 17A and 17B show images and graphs depicting that phagocytotic ability of microglia cells between WT and STAT1 deficient mice is similar. FIG. 17A shows images of microglia cells from WT or STAT1 deficient mice were incubated with florescent beads. Cells were fixed 5 mins after incubation and imaged for internalized beads. WT and KO medium are medium from WT or KO microglia cells respectively. FIG. 17B shows a graph depicting the quantification results of beads internalized.

FIG. 19A shows a graph depicting the body weight of APP/PS1 and APP/PS1/STAT1−/− mice at 3-month-old, n=5 for each group, respectively. FIG. 19B shows images of Oil-red-O staining of liver sections of APP/PS1 and APP/PS1/STAT1−/− mice, respectively. Images are representative of 3 pairs of mice. FIGS. 19C, 19D, 19E, and 19F shows four graphs depicting results of real-time PCR quantification of LPL, ABCA1, APOE, HMGCR in APP/PS1 and APP/PS1/STAT1−/− mice, respectively.

DETAILED DESCRIPTION OF THE INVENTION

Figure 1A:
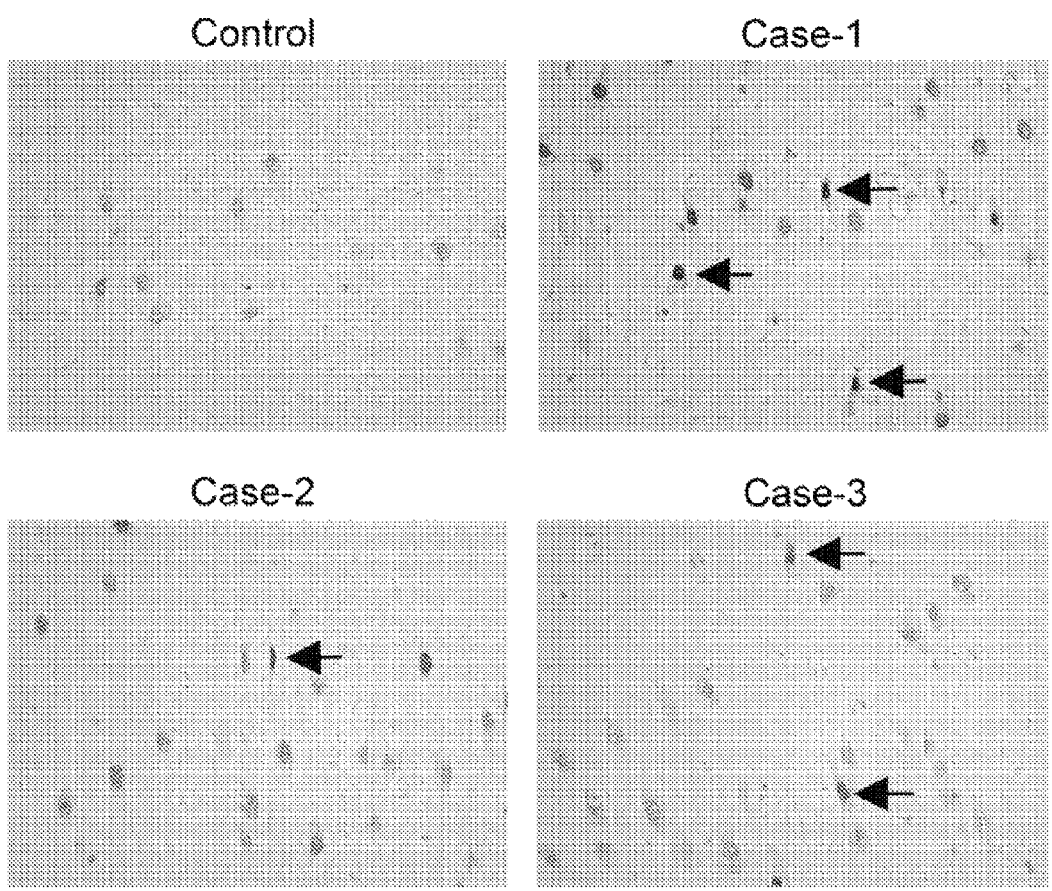
FIGS. 1A and 1B are images showing that elevated levels of phosphorylated STAT1 is detected in patients with Alzheimer's Disease.

The present disclosure is based, in part, on the new and surprising discovery that STAT1-regulated CH25H expression affects pathogenesis of Alzheimer's Disease (AD). The inventors discovered that CH25H was the downstream target of STAT1, and STAT1 and its target CH25H promoted Aβ deposition during AD development. Higher amount of pphophorylated STAT1 (pSTAT1) detected in AD patient was a causal event for AD development, because genetic depletion of STAT1 delayed Aβ deposition in the brain. CH25H is an enzyme that converts cholesterol to 25-OHC. One of the unique features of 25-OHC is that it can cross Blood-Brain-Barrier (BBB), which can be beneficial for drug development, as a number of drugs currently under clinical trial had problem with BBB penetration. The inventors demonstrated the effect of CH25H or 25-OHC on AD pathogenesis. CH25H knockout mice had reduced Aβ deposition which was comparable to STAT1 knockout. In contrast, administration of 25-OHC boosted Aβ deposition in the brain.

Described herein are the methods and means to treat or prevent diseases or medical conditions that are related, at least in part, to the STAT1-CH25H axis, which produces 25-OHC as an effector to regulate Aβ deposition. In such diseases or medical conditions, the activity of STAT1-CH25H is enhanced thereby resulting in an increase in Aβ deposition Enhancement of STAT1-CH25H activity may be due to, but not limited to: 1) increased STAT1 phosphorylation; 2) increased expression of STAT1 or CH25H; 3) increased cholesterol as substrate for CH25H. The antagonist herein for the treatment and prevention may be a chemical, a small molecule, a pharmaceutical, a non-coding RNA, an antisense nucleotide, a peptide, a protein or an antibody or portions thereof. In a particular embodiment, the antagonist is administrated in a therapeutically effective amount.

The present invention herein provides methods for treating diseases or medical conditions related to Aβ deposition in brain cells of a subject. In one embodiment, the diseases or medical conditions are due to abnormal production, transport or clearance of Aβ. In another embodiment, the diseases or medical conditions are due to increased activity of the STAT1-CH25H pathway caused by factors such as, but not limited to, IFNα, IFN-β, IFN-γ, IL-6 family cytokines, or conditions of acute or chronic inflammation. In a further embodiments, the diseases or medical conditions are due to increased amount of 25-OHC caused by high cholesterol amount in the subject.

The inventors found that blockade of STAT1 signaling, abrogation of STAT1 expression or depletion of CH25H attenuate pathogenesis of AD with reduced Aβ plaques. Chemical analog of 25-OHC also reduced APP in cultured cells. The methods of treatment herein include administrating an agent to modulate STAT1 or CH25H signaling, expression or activity, e.g., an agent to block 25-OHC activity or to promote 25-OHC degradation. In particular, the invention provides methods and means to treat Alzheimer's Disease.

Thus, in one aspect, the present invention is directed to methods for treating diseases like AD through in the brain of a subject by inhibiting STAT1, its downstream target CH25H, or 25-hydroxylated cholesterol (25-OHC).

Thus, in one aspect, the present invention is directed to methods for preventing or delaying the onset of diseases like AD in the brain of a subject by inhibiting STAT1, its downstream target CH25H, or 25-hydroxylated cholesterol (25-OHC).

In another aspect, the present invention is directed to methods for reducing amyloid-beta (Aβ) deposition in the brain of a subject by inhibiting STAT1, its downstream target CH25H, or 25-hydroxylated cholesterol (25-OHC).

In another aspect, the present invention is directed to methods for preventing or delaying the accumulation of amyloid-beta (Aβ) deposition in the brain of a subject by inhibiting STAT1, its downstream target CH25H, or 25-hydroxylated cholesterol (25-OHC).

In one embodiment, the inhibition of STAT1 in the above methods is by administration of to the subject a pharmaceutically effective amount of a STAT1 inhibitor.

The term "subject", as used herein, means an animal, preferably a mammal, and most preferably a human. In some instances, subjects may be grouped into different sub-groups according to the presence or absence of certain biomarkers. In other instances, subject may be groped into different subgroups abased on whether the amount of certain biomarkers is below or above a threshold. In either case, a sub-group may then be included or excluded for treatment in the present invention.

In some embodiments, the STAT1 inhibitor is a composition comprising a pharmaceutically effective amount of an active agent, e.g., a compound, a peptide, an antibody or fragment thereof, or a nucleic acid, and a pharmaceutically acceptable excipient.

An "excipient", "carrier", "pharmaceutically acceptable excipient", "pharmaceutically acceptable carrier" or similar terms mean one or more component(s) or ingredient(s) that is acceptable in the sense of being compatible with the other ingredients of invention compositions or formulations and not overly deleterious to the patient, animal, tissues or cells to which the STAT1 inhibitor composition or formulation is to be administered.

The terms "pharmaceutically effective amount", "effective dose" or the like with respect to a STAT1 inhibitor mean an amount of the STAT1 inhibitor that is sufficient to elicit a desired response, e.g., reducing Aβ deposition in a subject to which it is administered, e.g., a human, or to detectable modulation or amelioration of a molecular or cellular parameter or a clinical condition or symptom of AD. An effective amount, e.g., for human therapeutic use, may be a single dose or two or more subdoses of a STAT1 inhibitor administered in one day, or it may be administered as multiple doses over a period of time, e.g., over 1, 2, 3, 4 or about 7 days to about 1 year.

Determination of a therapeutically effective amount is well within the capability of those skilled in the art in light of the detailed disclosure provided herein. For example, the therapeutically effective amount or dose can be estimated initially from in vitro and cell culture assays. For another example, an effective dose may be formulated in animal models to achieve a desired concentration or titer. Such information can be used to more accurately determine useful doses in humans.

Toxicity of the active ingredients described herein may be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition.

Dosage amount and interval may be adjusted individually to blood levels of the active ingredient that are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations. Depending on the severity and responsiveness of the condition to be treated, dosing can be of a single or a plurality of administrations, with course of treatment lasting from several days to several weeks or until cure is effected or diminution of the disease state is achieved. The amount of a composition to be administered will, of course, be dependent on, for example, the subject being treated, the severity of the affliction, the manner of administration, and the judgment of the prescribing physician.

For example, in some embodiments, the pharmaceutically effective amount of STAT1 inhibitor may be as low as about 0.02 mg/kg/day to about 0.03 mg/kg/day in human, and as high as about 2 mg/kg/day to about 3 mg/kg/day. In still some embodiments, the effective amount may be higher than 3 mg/kg/day as the Aβ deposition becomes more severe. In other embodiments, the effective amount may be higher when the STAT1 inhibitor is used for treatment than when the STAT1 inhibitor is used for prevention or delaying the onset of Aβ deposition.

In some embodiments, the dosage and administration schedule may also depend on the gender of the human subject to be treated. In some instances, some female patients may be more prone to STAT1 treatment and therefore, dosage may be smaller and administration schedule may be less frequent than male patients. In other instances, some female patients may be more sensitive to STAT1 treatment and therefore, dosage may be smaller and administration schedule may be less frequent than male patients.

In some embodiments, the administration may preferably start early well before Aβ deposition can be detected. In other embodiments, the administration may start after Aβ deposition is detected but before any clinical symptoms of AD can be seen. In still other embodiments, the administration may start after clinical symptoms of AD can be seen. The administration may be for a single dose in some instances. The administration may be for multiple doses, e.g., 2, 3, 4, 5, or 6 doses in other instances. The administration may continue as many times as a medical doctor considers necessary.

In other embodiments, the administration schedule and the dosage may be related. For one example, when the period between the first administration started early before clinical symptom of AD can be seen, the dosage for each administration may be smaller than that where the first dose is administered after clinical symptoms of AD can be seen. For another example, when the administration is frequent, e.g., once every 12 hours, the dosage for each administration may be smaller than that where the administration is less frequent, e.g., once every 24 hours.

Terms such as "use", "treat", "treatment", "address" or the like in the context of using a STAT1 inhibitor in the treatment methods or other methods disclosed herein mean that the STAT1 inhibitor is administered to a subject, delivered to the subject's tissues or contacted with tissues, cells or cell free systems in vivo or in vitro, e.g., as described herein or a reference cited herein. Typically such use or treatment results in, e.g., (1) detectable improvement in or amelioration of the condition or symptom being treated, (2) detectable modulation in the activity, level or numbers of a relevant biomolecule, therapeutic cell population or a pathological cell population, (3) slowing of the progression of a condition or delaying its onset, or reduction of the severity of a symptom(s) of the condition or (4) another detectable response as described herein. Any such amelioration may be transient, e.g., lasting for at least a few, e.g., about 1 to 24, hours or days, e.g., about 1, 2, 3, 4, 5, 6 or 7 days, or amelioration may be prolonged, e.g., lasting about 8, 9, 10, 11, 12, 13, 14, 15, 16, 17, 18, 19, 20, 21, 22, 24, 26, 28, 35, 42, 49, 56 to about 60 days or more, or amelioration may be permanent. A treatment may slow the progression of a disease or symptom or it may reduce the severity thereof, e.g., onset of a disease or a symptom may be delayed in at least some subjects for about 1-24 hours, about 2-10 days, about 2-30 days or for about 1-5 years compared to subjects who are not treated with sufficient amounts of a STAT1 inhibitor. Thus, a use or treatment with a STAT1 inhibitor typically results in detectable modulation in a relevant immune parameter such as modulation of the level, activity or relative amount of a target effector or suppressor cell population, interleukin, cytokine, chemokine, immunoglobulin compared to a suitable control, e.g., untreated. A STAT1 inhibitor treatment can also cause modulation of the level or activity of a relevant transcription factor, enzyme, cell biological activity or level or activity of the etiological agent of the disease. A treatment with a STAT1 inhibitor may be used to delay or prevent the onset of a disease, symptom or complication or to ameliorate or slow the progression of a preexisting disease, condition, symptom or complication, or to facilitate elimination of a disease, condition, symptom or complication, e.g., the Aβ deposition in AD.

"Ameliorate", "amelioration", "improvement" or the like means a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with a STAT1 inhibitor, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after a STAT1 inhibitor is administered to a subject or is used in an assay or other method described herein or a cited reference, e.g., within about 1 hour of the administration or use of a STAT1 inhibitor to about 3, 6, 9 months or more after a subject(s) has received a STAT1 inhibitor.

The "modulation" of, e.g., a symptom, level or biological activity of a molecule, cellular response, cellular activity or the like, means that the cell, level or activity, or the like is detectably increased or decreased. Such increase or decrease may be observed in treated subjects as compared to subjects not treated with a STAT1 inhibitor, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after a STAT1 inhibitor is administered to a subject or is used in an assay or other method described herein or a cited reference, e.g., within about 1 hour of the administration or use of a STAT1 inhibitor to about 3, 6, 9 months or more after a subject(s) has received a STAT1 inhibitor.

At various locations in the present disclosure, e.g., in any disclosed embodiments or in the claims, reference is made to compounds, compositions, formulations, or methods that "comprise" one or more specified components, elements or steps. Invention embodiments also specifically include those compounds, compositions, formulations or methods that are or that consist of or that consist essentially of those specified components, elements or steps. The terms "comprising", "consist of" and "consist essentially of" have their normally accepted meanings under U.S. patent law. For example, disclosed compositions or methods that "comprise" a component or step are open and they include or read on those compositions or methods plus an additional component(s) or step(s). Similarly, disclosed compositions or methods that "consist of" a component or step are closed and they would not include or read on those compositions or methods having appreciable amounts of an additional component(s) or an additional step(s).

In some instances, the STAT1 inhibitor may be an antibody against an interferon because interferons are required for the activation of STAT1 and the inhibition of interferons would prevent or reduce the activation of STAT1. An example of interferon antibodies is Fontolizumab (planned trade name HuZAF), a humanized monoclonal antibody to interferon-γ. Similar antibodies to interferons may be made and screened for its inhibitory effects on interferons by a person skilled in the art since methods of making and assaying antibody activities are generally known in the art.

In some instances, the STAT1 inhibitor may be an antibody against an interferon receptor because interferon receptors are required for the activation of STAT1 and the inhibition of interferon receptors would prevent or reduce the activation of STAT1. An example of interferon receptor antibodies is Anifrolumab, a Human monoclonal antibody targeting type I interferon (IFN) receptor 1. Similar antibodies to interferon receptors may be made and screened for its inhibitory effects on interferon receptors by a person skilled in the art since methods of making and assaying antibody activities are generally known in the art.

In some instances, the STAT1 inhibitor may be an antibody against an IL6 because IL6 are required for the activation of STAT1 and the inhibition of interferons would prevent or reduce the activation of STAT1. An example of IL-6 antibodies is Siltuximab, is a chimeric (made from human and mouse proteins) monoclonal antibody against IL-6. Similar antibodies to IL-6 may be made and screened for its inhibitory effects on IL-6 by a person skilled in the art since methods of making and assaying antibody activities are generally known in the art.

In some instances, the STAT1 inhibitor may be an antibody against an IL-6 receptor (IL-6R) because interferon receptors are required for the activation of STAT1 and the inhibition of IL-6 receptors would prevent or reduce the activation of STAT1. An example of IL-6 receptor antibodies is Tocilizuma, a humanized monoclonal antibody against the interleukin-6 receptor. Similar antibodies to IL-6R may be made and screened for its inhibitory effects on IL-6R by a person skilled in the art since methods of making and assaying antibody activities are generally known in the art.

In still other instances, the STAT1 inhibitor may be an agent the STAT1 inhibitor may be an agent that inhibits JAK1 or JAK3, because JAK1 and JAK3 are well known upstream kinases that activate STAT signaling. Agents that inhibit JAK1 and JAK3 may be small molecules, for example, Filgotinib used as JAK1 inhibitor, Tofacitinib for JAK3 inhibitor.

In still other instances, the STAT1 inhibitor may be an agent that reduces STAT1 phosphorylation. Such agents that reduce STAT1 phosphorylation may be FLLL32 that was reported to inhibit STAT phosphorylation.

In still other instances, the STAT1 inhibitor may be an agent that prevents the translocation of STAT1 into nucleus. Such agents that prevent the translocation of STAT1 into nucleus may be Meales virus protein P and V.

In still further instances, the STAT1 inhibitor is an RNAi agent against STAT1. such RNAi agent may be any SiRNA targeting STAT1, for example, product 105153 from ThermoSisher Scientific. Other siRNA agents target STAT1 can be made by a skilled person in the art because methods of making siRNA for a specific target is generally known in the art.

In still further instances, as a method for treatment, prevention, or delaying the onset of AD a genome editing tool may be used to delete the entire STAT1 gene, the phosphrylation site of the STAT1 gene, the promoter region of the STAT1 gene, or the SH2 domain of the STAT1 gene in neural cells. The genome editing tool can be any genome editing tool as long as it can be used to target the specific regions of STAT1 gene and can be delivered to cells of interest. One example of such genome editing tool is the CRISPR-CAS9 system as described in Ran, F. et al. In vivo genome editing using *Staphylococcus aureus* Cas9, Nature (2015). Another example of such genome editing tool is the CRISPR-Cpf1 system as described in Zetsche et al., Cpf1 Is a Single RNA-Guided Endonuclease of a Class 2 CRISPR-Cas System, Cell (2015).

In other embodiments, the inhibition of CH25H in the above methods is by administering to the subject a pharmaceutically effective amount of a CH25H inhibitor. In some embodiments, the CH25H inhibitor is a STAT1 inhibitor because STAT1 activates CH25H and the inhibition of STAT1 results in the inability of STAT1 to activate CH25H. STAT1 inhibitors may be any STAT1 inhibitor disclosed in this application.

In other embodiments, as a method for treatment, prevention, or delaying the onset of AD a genome editing tool may be used to delete the entire CH25H gene, the histine cluster regions of the CH25H gene, or the promoter region of the CH25H gene in neural cells. The genome editing tool can be any genome editing tool as long as it can be used to target the specific regions of CH25H gene and can be delivered to cells of interest. One example of such genome editing tool is the CRISPR-CAS9 system as described in Ran, F. et al. In vivo genome editing using *Staphylococcus aureus* Cas9, Nature (2015). Another example of such genome editing tool is the CRISPR-Cpf1 system as described in Zetsche et al., Cpf1 Is a Single RNA-Guided Endonuclease of a Class 2 CRISPR-Cas System, Cell (2015).

In other embodiments, the inhibition of 25-OHC in the above methods is by administering to the subject a pharmaceutically effective amount of a 25-OHC inhibitor.

In some instances, the 25-OHC inhibitor may be an CH25H inhibitor or a STAT1 inhibitor because CH25H and STAT1 are upstream to 25-OHC and the inhibition of either CH25H or STAT1 results in the inability of CH25H to produce 25-OHC. In other instances, the 25-OHC inhibitor may be an analog of 25-OHC. In still other instances, the 25-OHC inhibitor may be a 3-hydroxy-3-methyl-glutaryl-coenzyme A (HMG-CoA) reductase inhibitor. On example of the HMG-CoA reductase inhibitor is simvastatin.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It should be understood that this invention is not limited to the particular methodologies, protocols and reagents, described herein, which may vary. The terminology used herein is for the purpose of describing particular embodiments only, and is not intended to limit the scope of the present invention.

Examples of the disclosed subject matter are set forth below. Other features, objects, and advantages of the disclosed subject matter will be apparent from the detailed description, figures, examples and claims. Methods and materials substantially similar or equivalent to those described herein can be used in the practice or testing of the presently disclosed subject matter. Exemplary methods and materials are now described as follows.

EXAMPLES

Methods

Mice

APP/PS1 5XFAD mice were purchased from Jackson lab and the STAT1 deficient mice were provided by Daved Levy. CH25H KO mice were generated by crisper/cas9 method. The pST1374-Cas9-N-NLS-flag-linker plasmid (Addgene ID44758) used to express Cas9 protein, was described previously (Zhou et al., 2014). The Ch25 h gene sequence was downloaded from the UCSC Genome Browser website (http://genome.ucsc.edu/). Two sgRNA oligos were synthesized and annealed to the pUC57-sgRNA construct. In vitro transcription was performed as described previously (Zhou et al., 2014). The Cas9 mRNA and sgRNA were injected in the background of C57BL6/J. APP/PS1 mice were mated with CH25H−/− mice to generate off-springs that carry the APP/PS1 gene and either WT or KO allele for CH25H. APP/PS1 mice were mated with STAT1−/− mice to generate off-springs that carry the APP/PS1 gene and either WT or KO allele for STAT1. All mice were on a C57BL/6 genetic background and housed under specific-pathogen-free conditions at National University of Singapore. All experiments were performed with mice 3-4 months old and approved by the Institutional Animal Care and Use Committee of NUS.

Tissue Lysate Preparation and Sucrose Gradient

Mice brains were weighted and homogenized in 9 times volume of TBS. The resulting homogenate were centrifuged at 1000 g for 15 min at 4° C. Supernatant was taken as the post nuclear fraction. The post nuclear fraction was laid carefully to a 5%-45% sucrose gradient, and centrifuged at 147,000 g for 16 hour at 4° C. After centrifuge, lml was taken as each fraction from top to the bottom. Triton was added to each fraction to reach a final concentration of 0.1% in order to dissolve membrane associated protein. The resulting samples were used for western blot analysis.

Exosome Preparation

SH-SY5Y cells over-express human APP were cultured in DMEM with 10% FBS. One day before exosome preparation, medium was changed to blank DMEM to avoid the contamination of serum exosomes. 24 hour after medium change, the mediums were collected, and spin at 200 g for 5 min to pellet down floating cells. The cell free medium was further centrifuged at 100,000 g for 1 h at 4° C., and the pellet containing exosomes was dissolved in RIPA buffer Microarray Analysis Microarray analysis was performed using affymetrix microarray system (Affymetrix) serviced by Molecular Genomics. Data analysis was performed with GeneSpring software. Differentially expressed genes were used as input in the David Functional Annotation Clustering website: (http://david.abcc.ncifcrf.gov/home.jsp), using the default setting of the medium classification stringency. Results of clustering were replotted in pie graph.

Histological Analysis

Tissues were fixed in 4% paraformaldehyde, dehydrated, penetrated and paraffin embedded. Sections (5 μm) were stained with hematoxylin and eosin (H&E) to assess general morphology. For immunofluorescence (IF) or immunohistochemistry (IHC), sections were rehydrated and stained with primary antibody against Aβ (Cell signaling), followed by incubation with fluorescence-conjugated secondary antibodies (Invitrogen). For Oil red O staining, livers were embedded in Tissue Tek (Electron Microscopy Sciences) and frozen at −80° C. 10 μm thick sections were cut and hydrated with dH2O, followed by incubation in Oil Red O working solution (0.3% Oil Red O (Sigma) in 60% isopropanol) for 1 h. After that, slides were quickly washed in 60% isopropanol three times until isopropanol dripping off the slides was clear. Subsequently, the slides were washed with $H_2O$ and counter stained with haematoxylin.

Real-Time PCR

Total RNA was extracted from cells with Trizol reagent (Invitrogen) according to the manufacturer's instruction. Complementary DNA (cDNA) was synthesized with Superscript reverse transcriptase (Invitrogen). Gene expressions were measured by 7500 real-time PCR system (Applied Biosystems) with SYBR qPCR kit (KAPA). Actib, Gapdh or Rn18S was used as internal control. The primer sequences are available upon request.

ELISA

Quantification of Aβ42 was carried out with ELISA kit (Millipore) according to the manufactures' instructions.

Chromatin Immunoprecipitation Assays

Half of the brain hemisphere from APP/PS1 or APP/PS1/STAT1−/− mice were homogenized in 9 times volume of TBS to obtain brain homogenate. Crosslink was performed by addition of formaldehyde at final concentration of 1% for 10 min followed by quenching with Glycine. The homogenate were treated with hypotonic buffer followed by nuclear lysis buffer to release chromatin. The chromatin were fragmented by sonication and precleared with protein G beads, and subsequently precipitated with anti-STAT1 antibody (Santa Cruz) or normal rabbit IgG (Santa Cruz) overnight at 4° C. After washing and elution, crosslink reversal was done by incubating at 65° C. for 8 hr. The eluted DNA was purified and analyzed by RT-PCR with primers specific to CH25H promoter as described previously.

Statistics

Statistical significance was determined by Student's t test using GraphPad Prism 6.01. The p value<0.05 was considered significant. The p values of clinical scores were determined by one-way multiple-range analysis of variance (ANOVA) for multiple comparisons. Unless otherwise specified, data were presented as mean and the standard error of the mean (mean±SEM).

Example 1 Stat1 Knockout Mice had Reduced Aβ Deposition

Figure 1B:
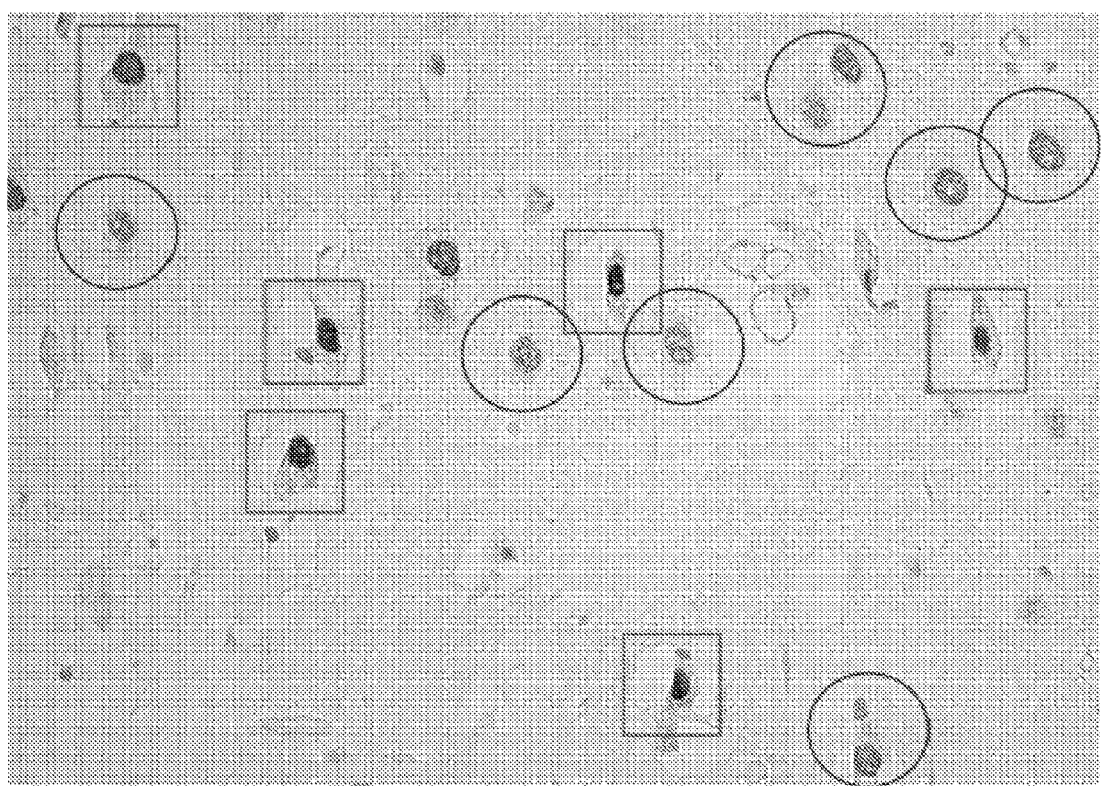

We demonstrated the expression of STAT1 was higher in AD cases than the aged matched control cases (FIGS. 1A and 1B). In FIG. 1A, no staining of Phosphorylated STAT1 (pSTAT1) was seen in the control cells. In contrast, as shown in the same FIG. 1A and the enlarged snapshot of the photo of Case-1 in FIG. 1B, much more staining of pSTAT1 was seen in each of the three cases.

Figure 2A:
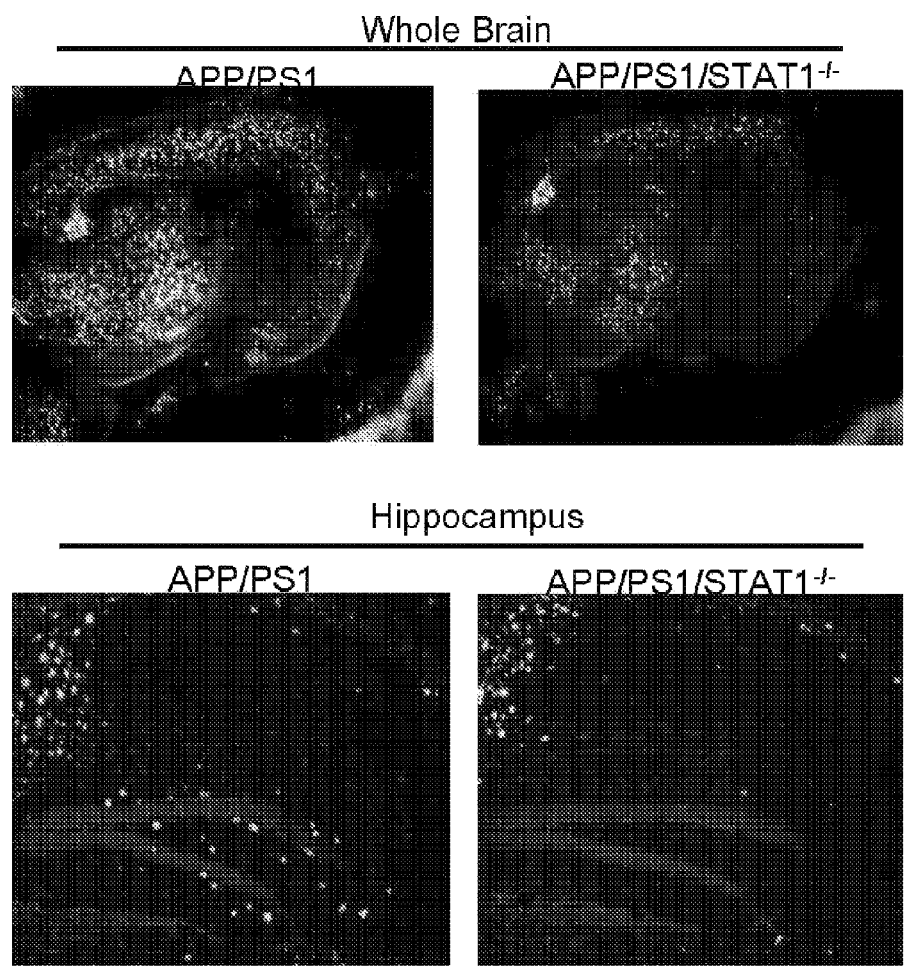
FIGS. 2A-2E are images and graphs showing STAT1 gene deficiency attenuates amyloid-beta deposition in the brain.
Figure 2B:
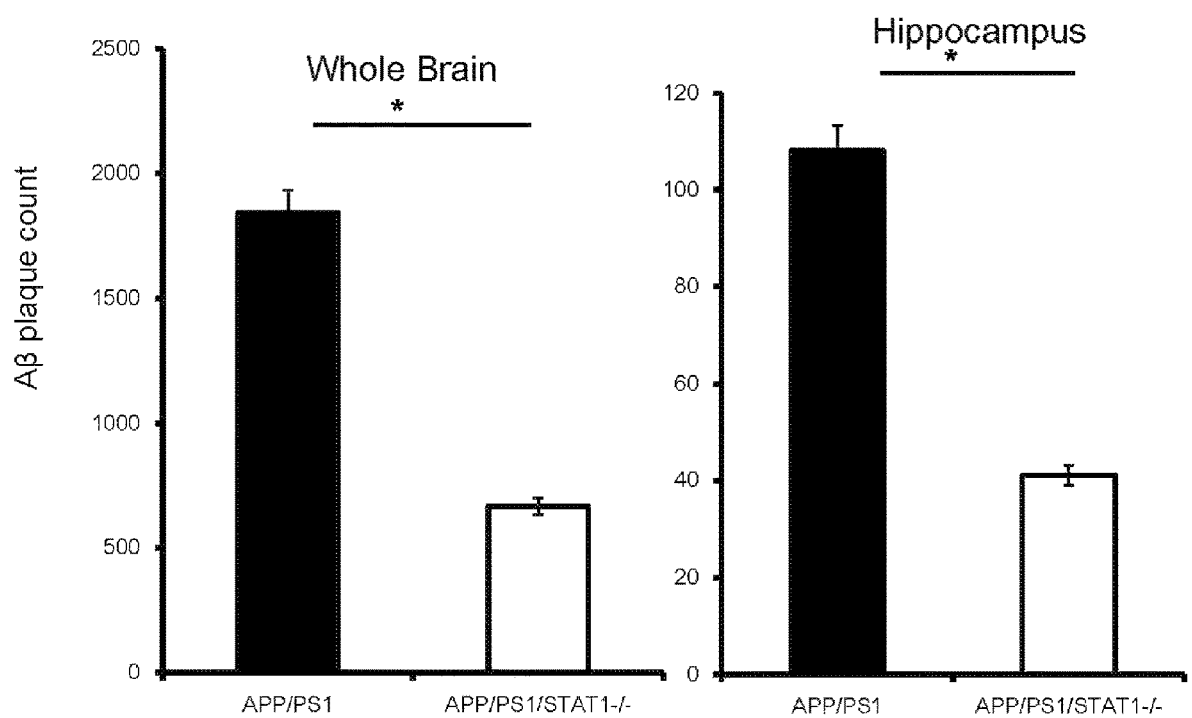
Figure 2C:
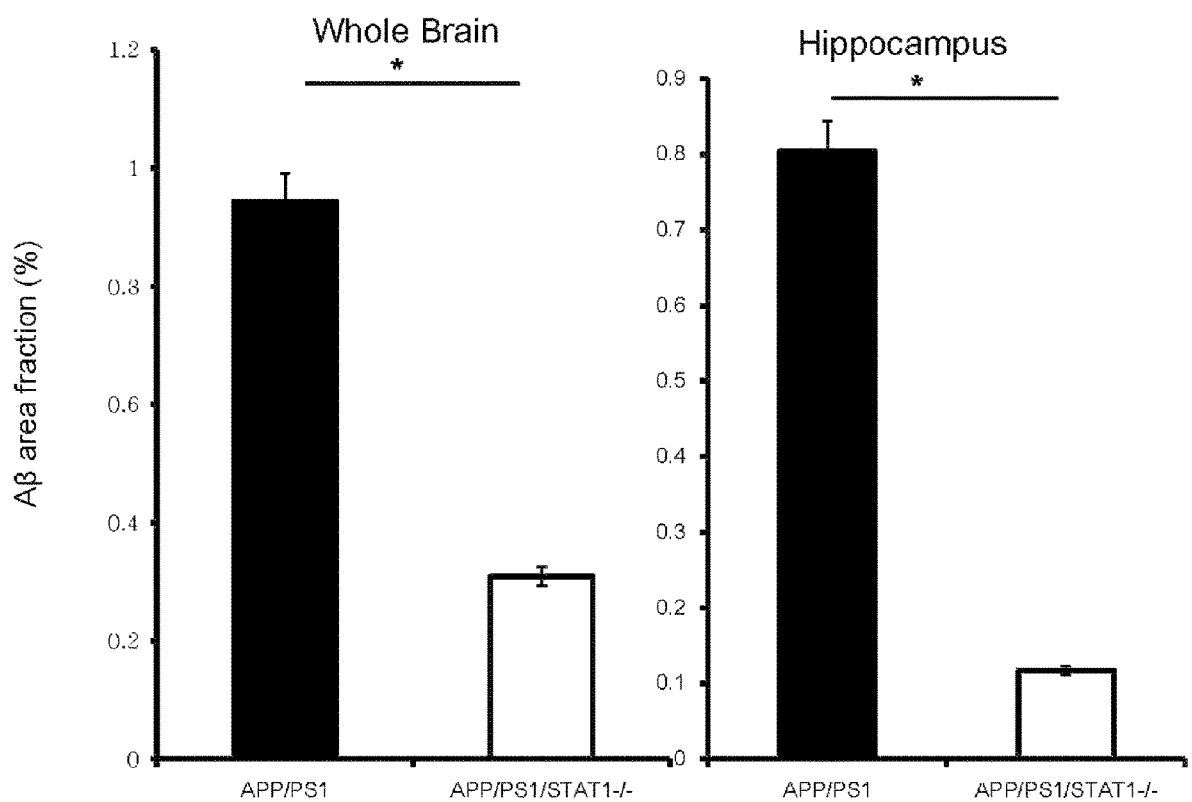
Figure 2D:
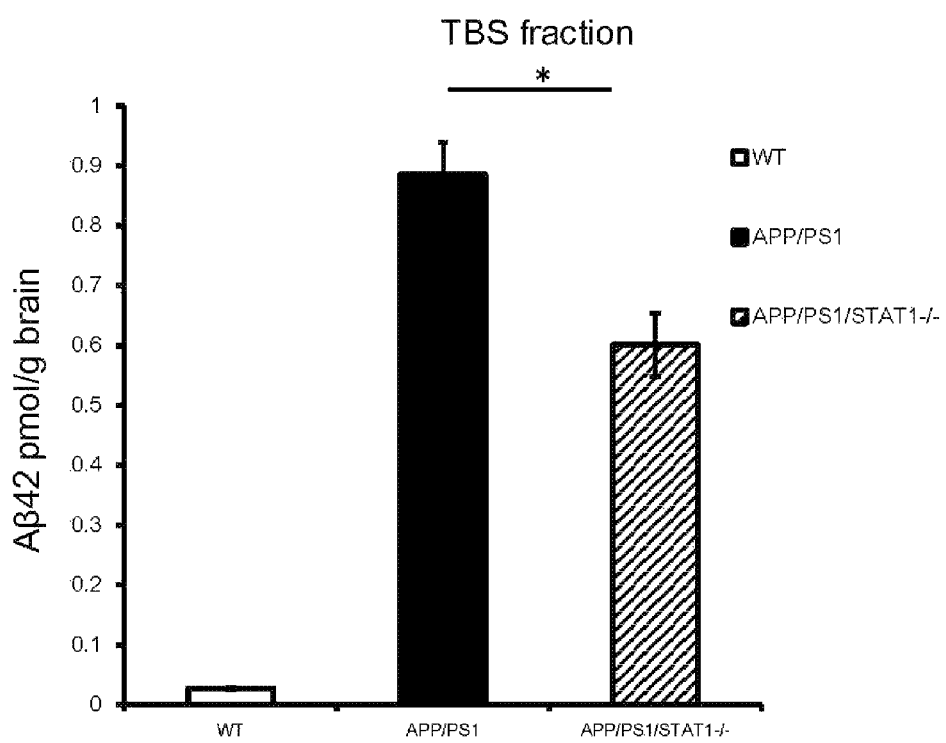
Figure 2E:
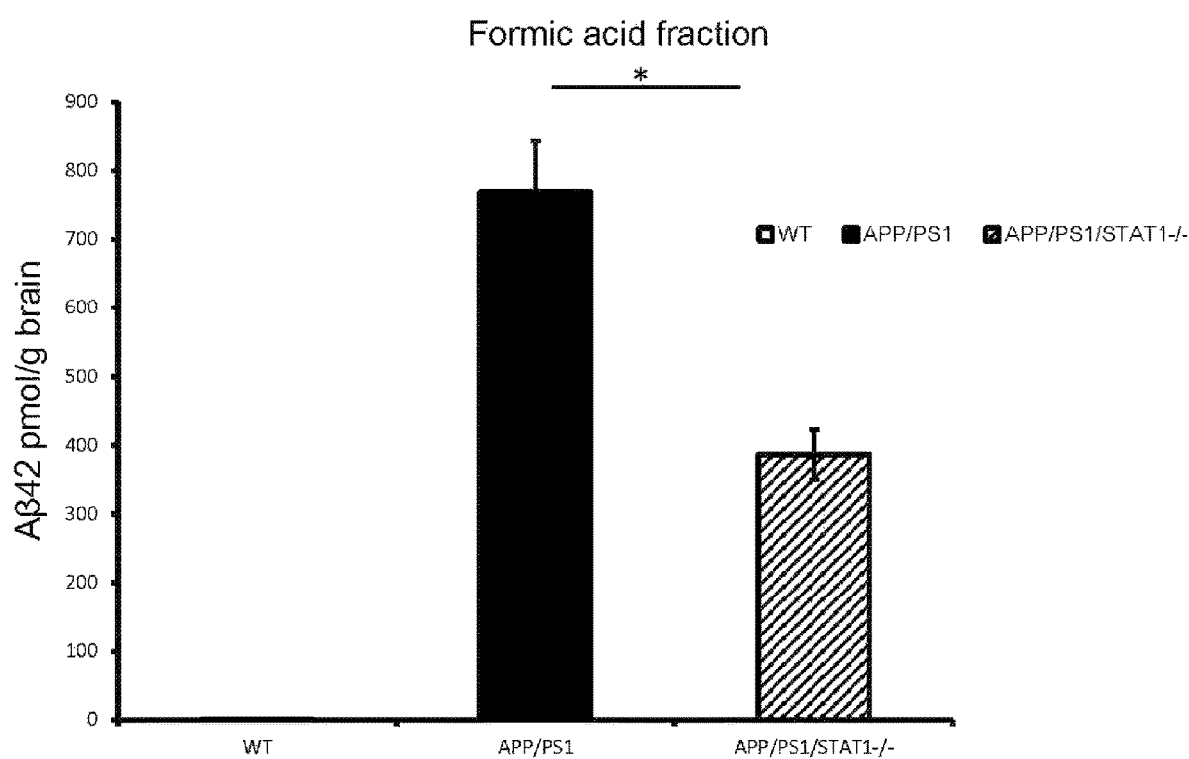
Figure 16A:
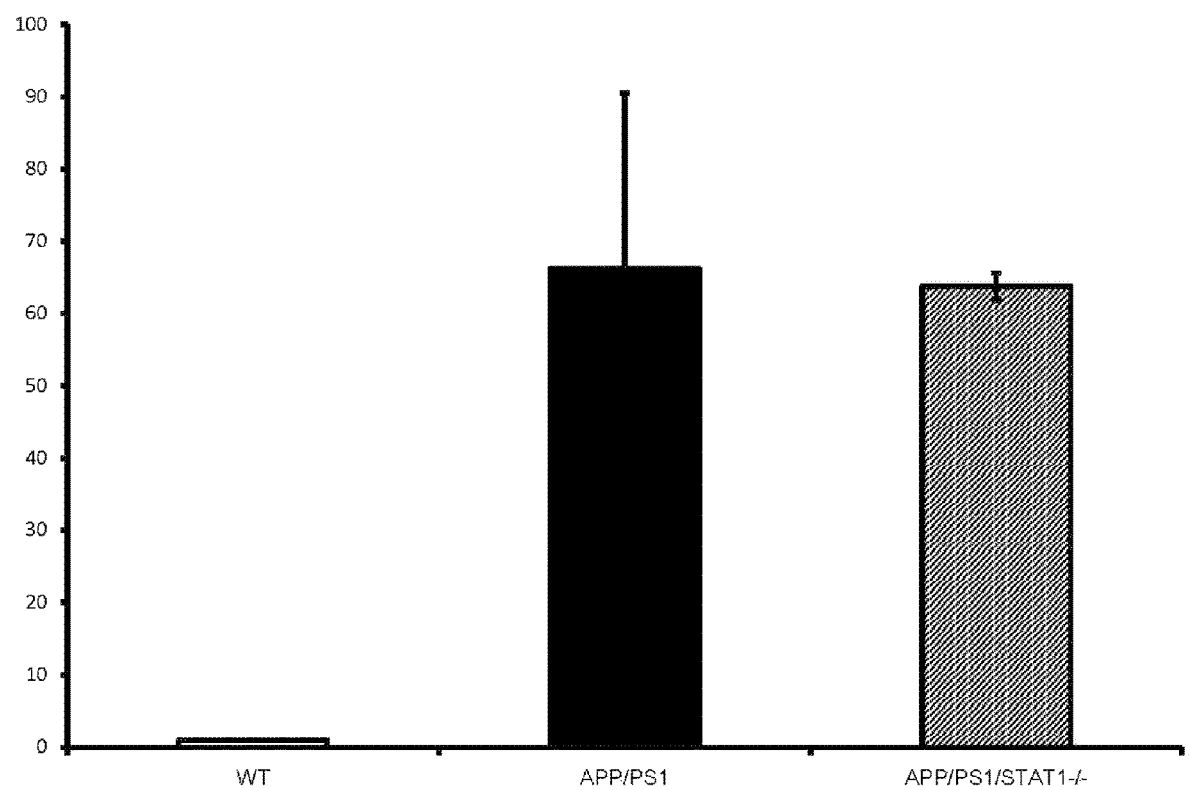
FIGS. 16A, 16B, 16C and 16D show graphs depicting the difference in Aβ deposition being not due to difference in APP expression level or the secretases that cleavages APP.
Figure 16B:
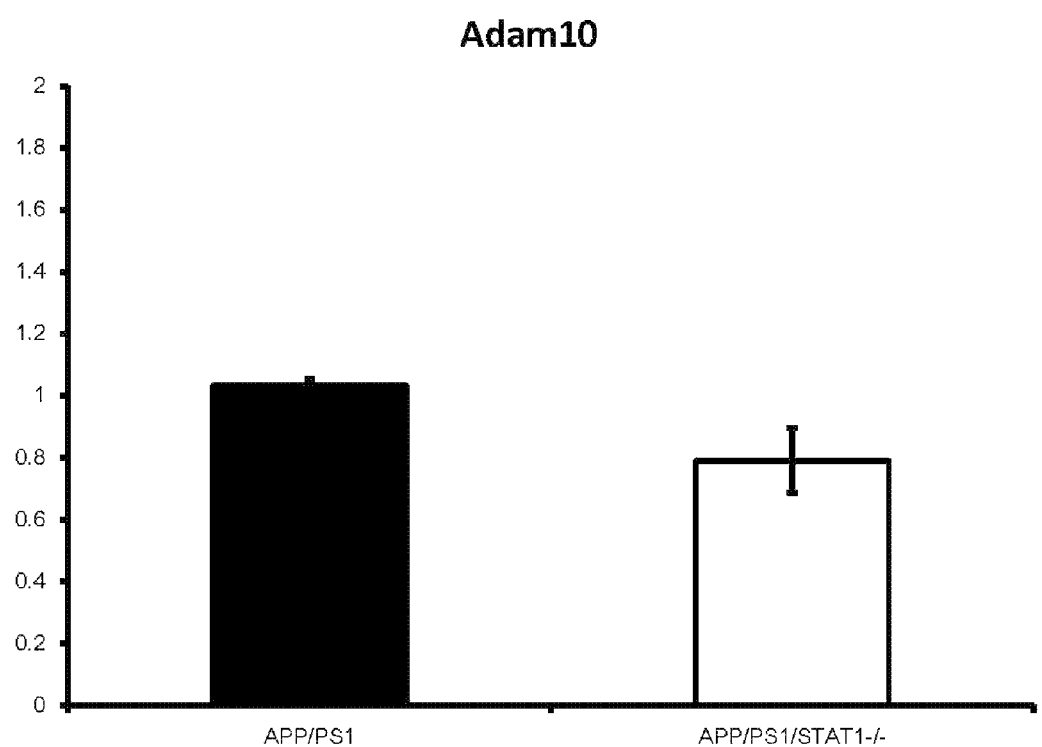
Figure 16C:
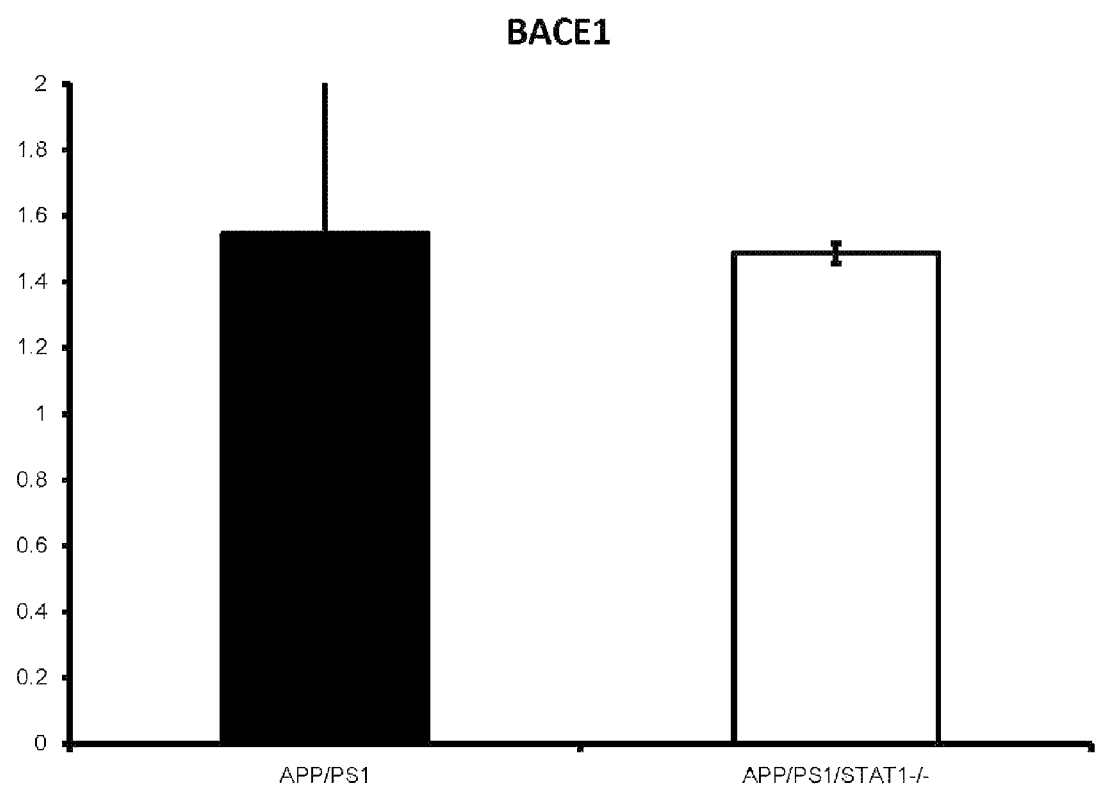
Figure 16D:
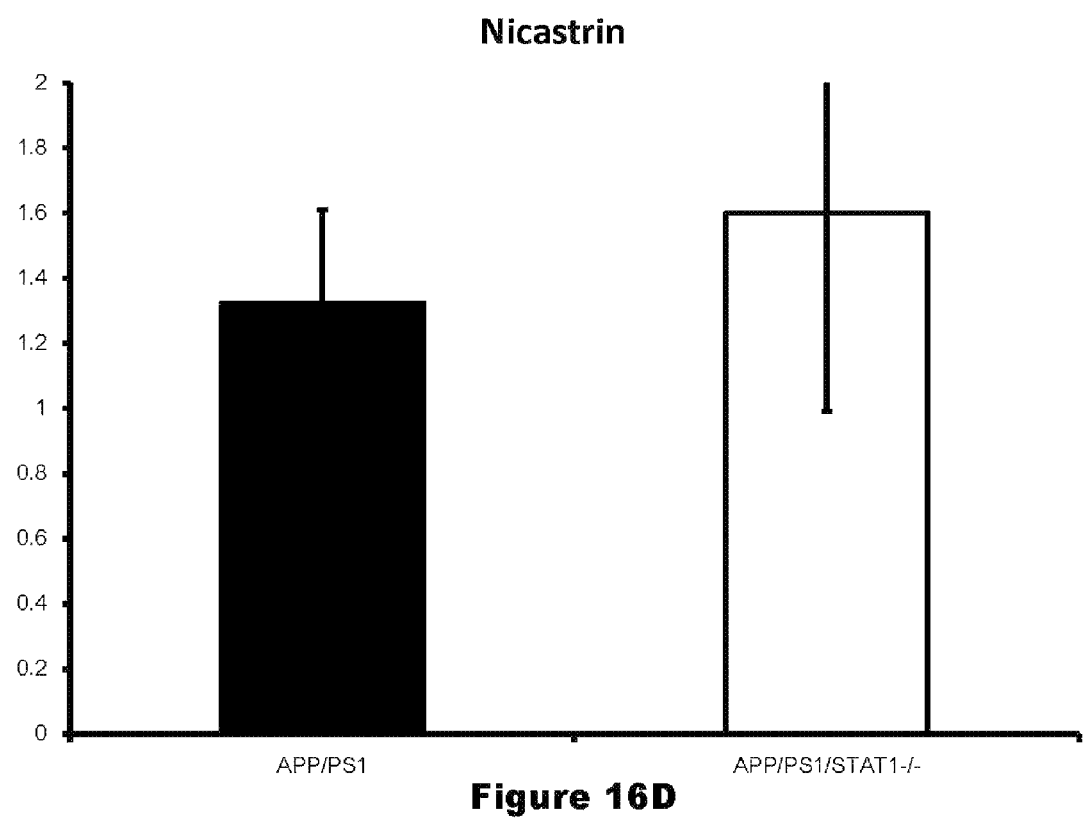

To understand whether the activation of STAT1 pathway was causal for the pathogenesis of AD, or was an consequence of neuro-inflammation in late stage of AD, we crossed STAT1−/− mice with APP/PS1 mice to generate AD mice with STAT1−/− background. APP/PS1/STAT1−/− mice, and their littermate controls of APP/PS1 genotype were kept to 3-4 months and sacrificed for histological examination of Aβ deposition. Surprisingly, we found consistent reduction in Aβ number as well as areas occupied by Aβ in Stat1−/− mice (FIGS. 2A and 2B), Similar results were observed when we measure Aβ42 in TBS or formic acid extraction (FIGS. 2C and 2D). Furthermore, the reduction in Aβ was not due to change in APP expression level, or the secretase cleavages APP (FIGS. 16A and 16B).

Figure 3A:
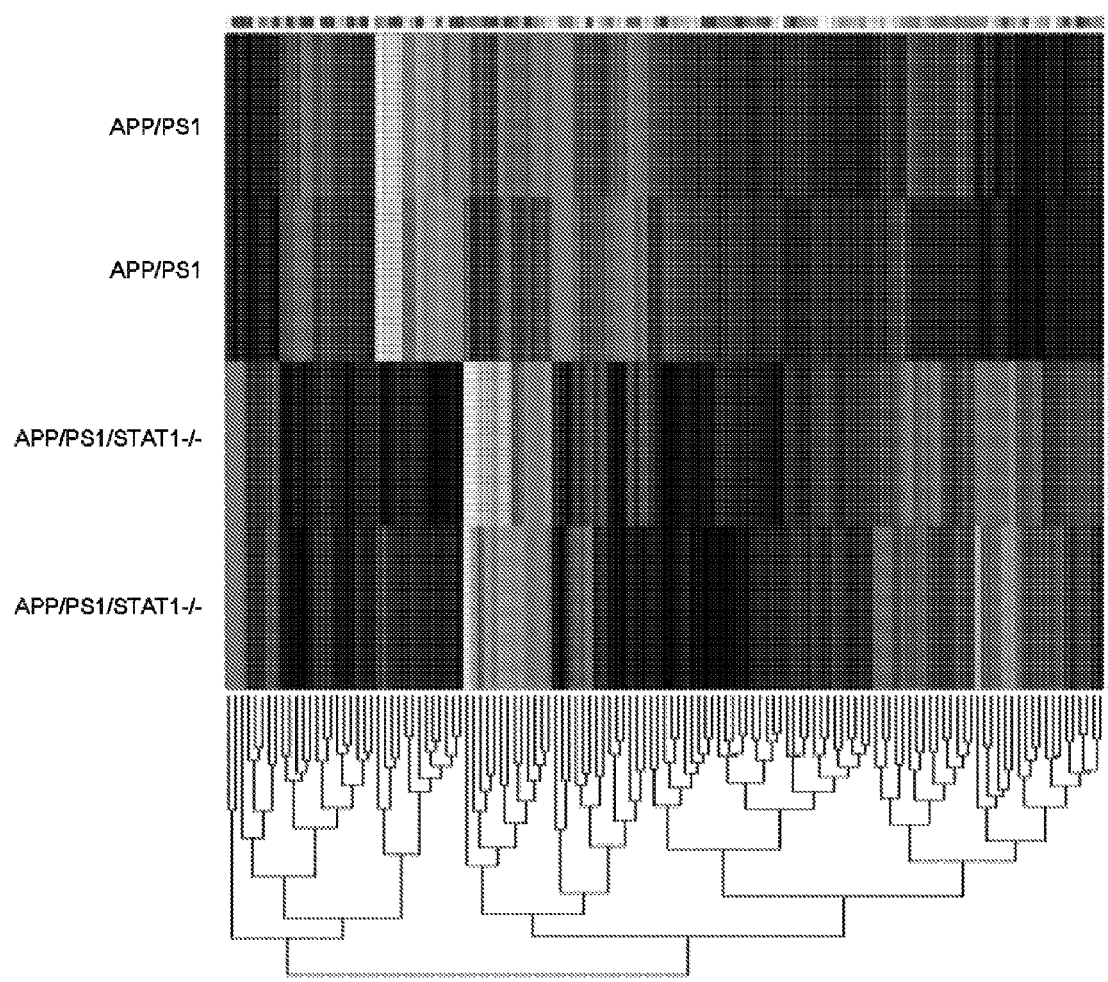
FIGS. 3A and 3B show graphs depicting the identification of CH25H as STAT1 downstream target. Specifically.
Figure 3B:
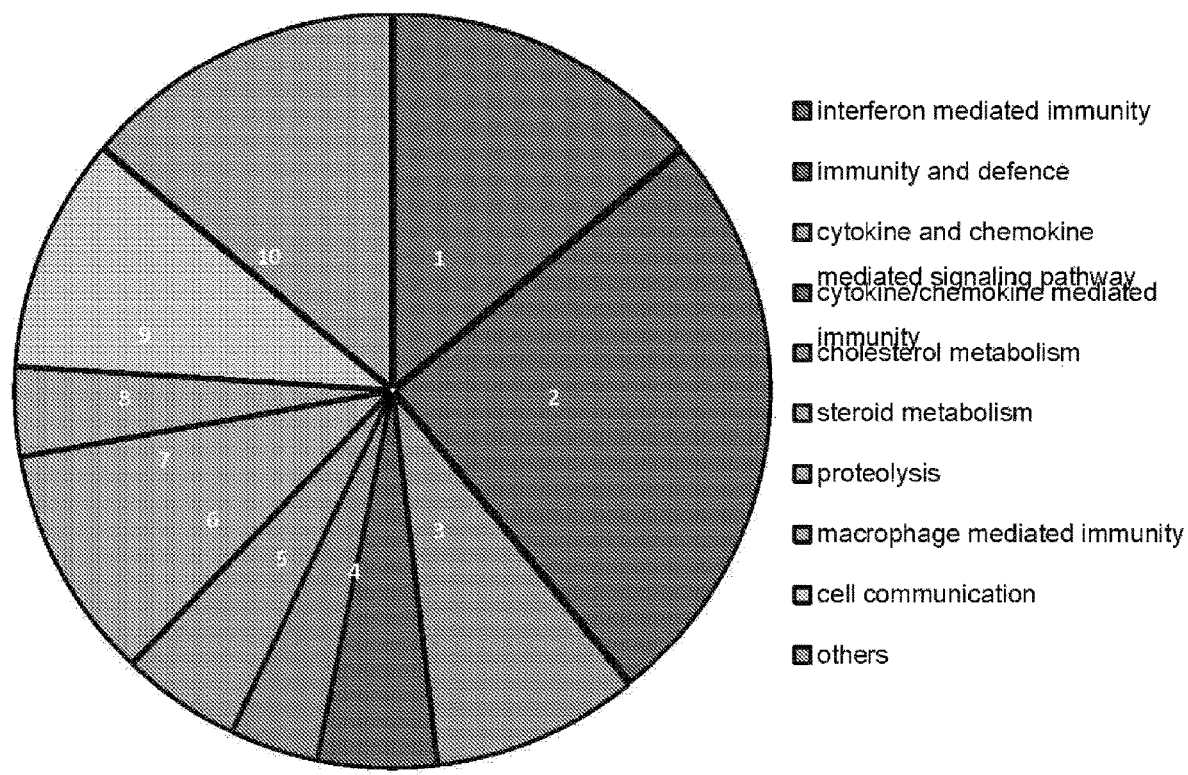
Figure 4A:
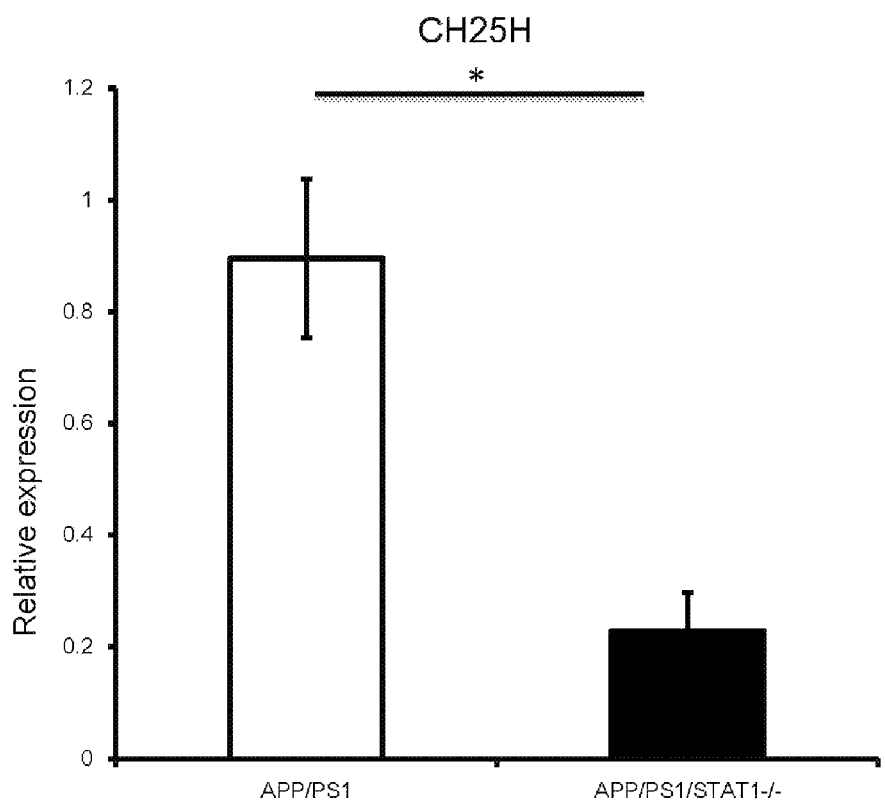
FIGS. 4A and 4B shows a graph and images depicting that CH25H is reduced in STAT1 deficient mice, respectively. Specifically.
Figure 4B:
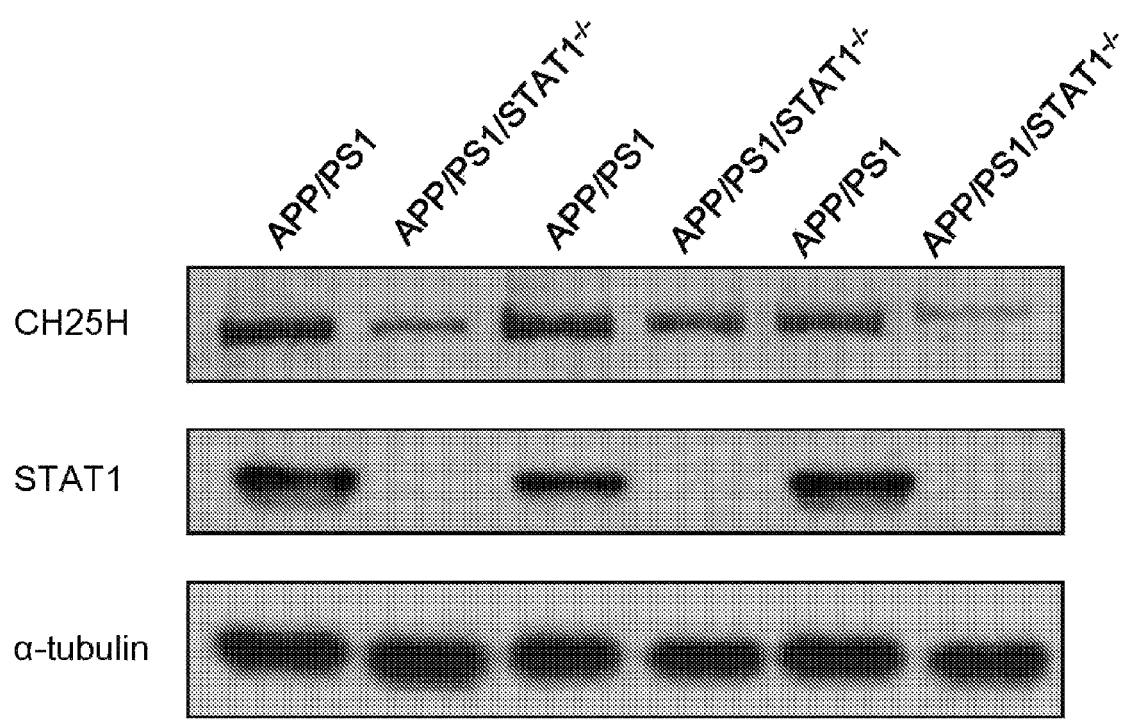
Figure 5A:
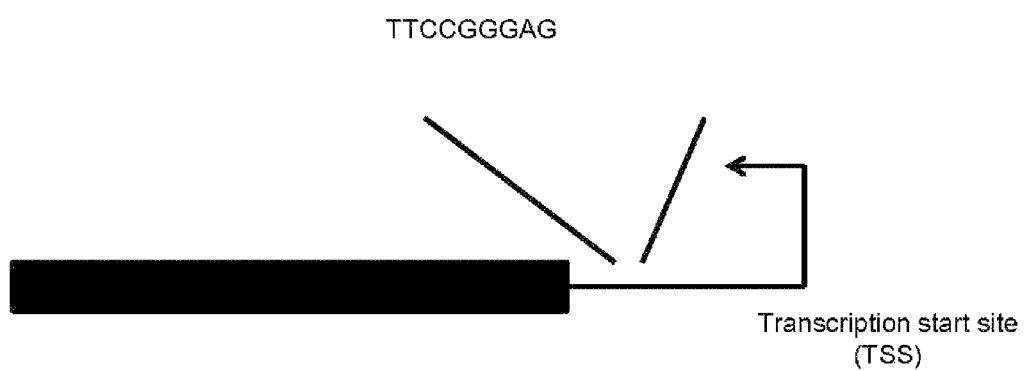
FIGS. 5A and 5B show graphs depicting that STAT1 physically binds to CH25H promoter. Specifically.
Figure 5B:
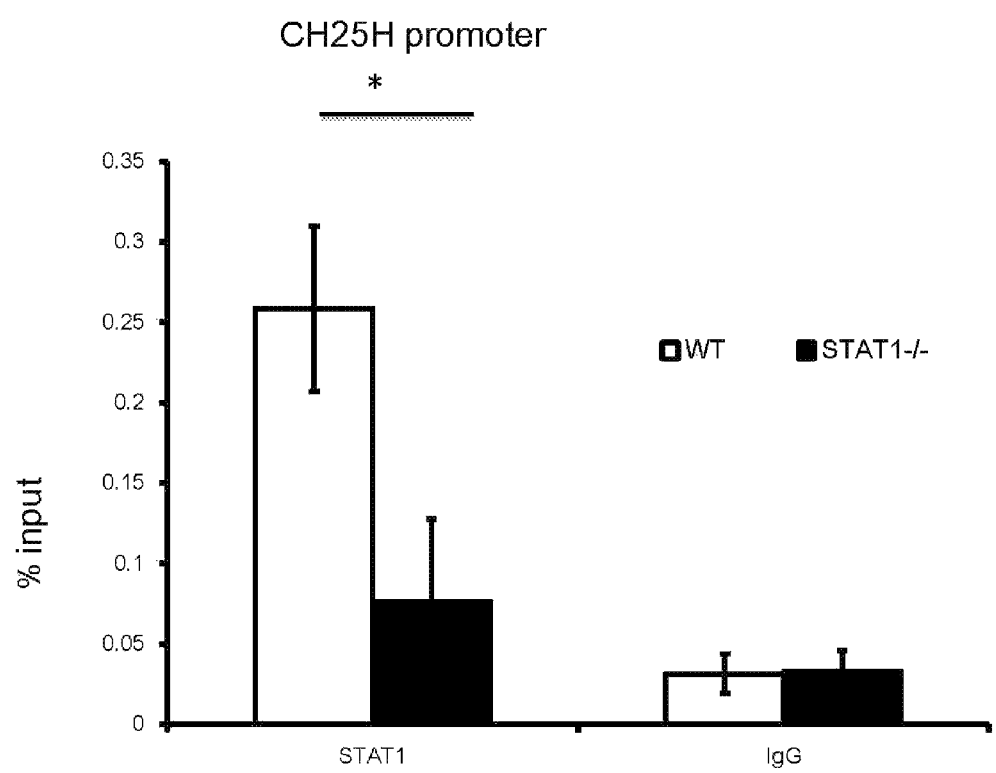
Figure 6A:
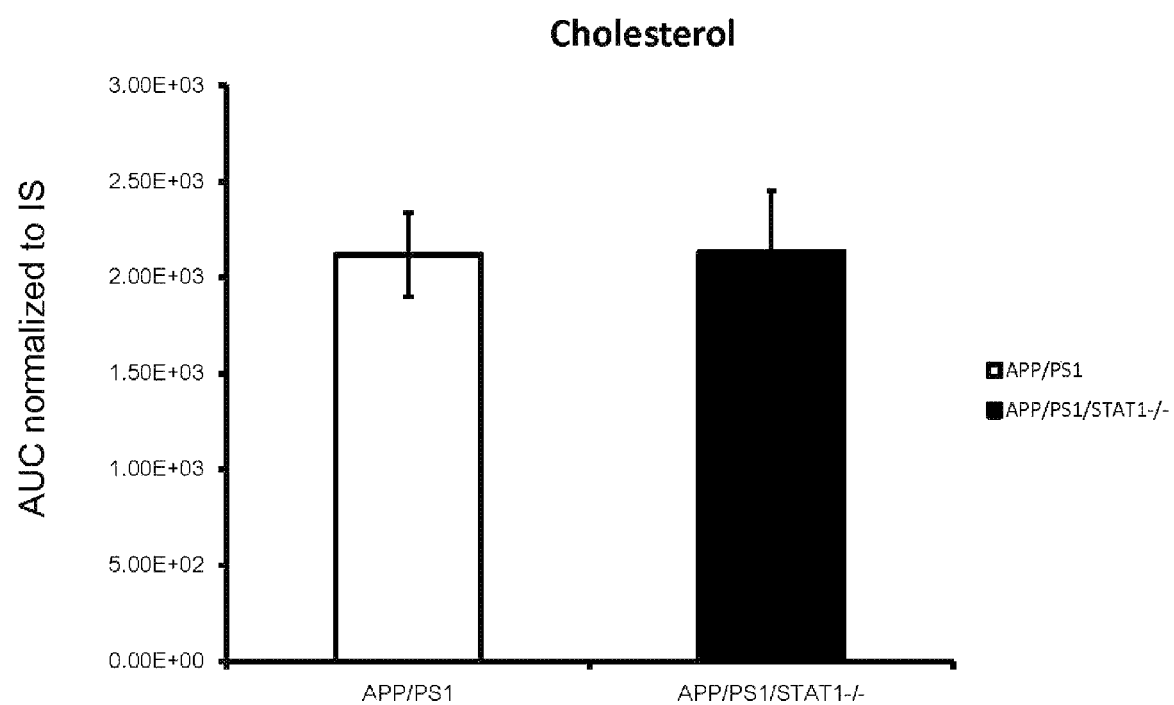
FIGS. 6A and 6B shows graphs depicting that STAT1 deficiency leads to reduced 25-OHC in the brain. Specifically.
Figure 6B:
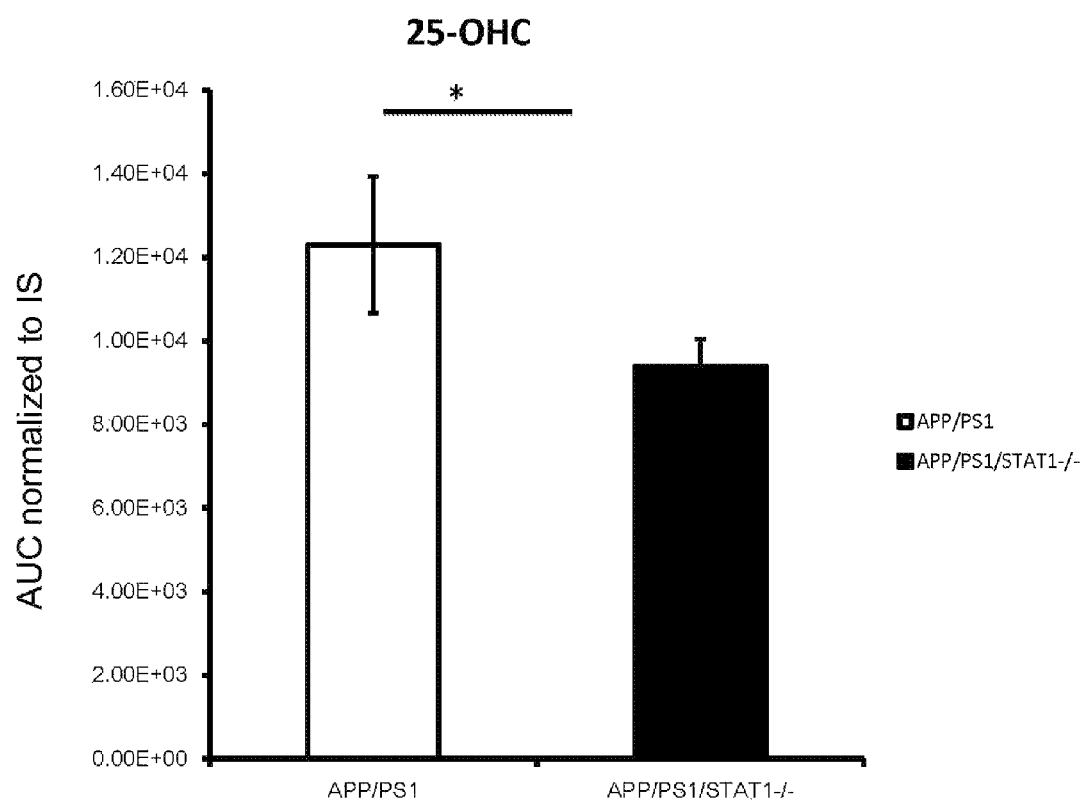

Example 2 Reduced Aβ Deposition in Stat1-KO Mice was Due to the Reduction of its Downstream Target CH25H Our microarray data identified CH25H as a STAT1-regulated gene in AD conditions (FIGS. 3A and 3B). Furthermore, we confirmed the regulatory effect of STAT1 on CH25H by real-time PCR, Western Blot and ChIP assay (FIGS. 4A,4B,5A,5B). As shown in FIG. 4A which depicts real-time PCR results, CH25H mRNA expression is significantly reduced in STAT1 deficient mice. As shown in FIG. 4B which depicts Western Blot results, CH25H protein level is also significantly reduced in STAT1 deficient mice. Results from the ChIP assay in FIGS. 5A and 5B also showed that in STAT1 deficient mice, less STAT1 was binding to the CH25H gene promoter sequence. The reduced level of 25-OHC in STAT1 deficient mice further supported the notion that STAT1-CH25H axis controls brain 25-OHC level (FIG. 6A-6B).

Example 3 STAT1-CH25H Regulated 25-OHC Affects APP Secretion in Exosomes

Figure 7:
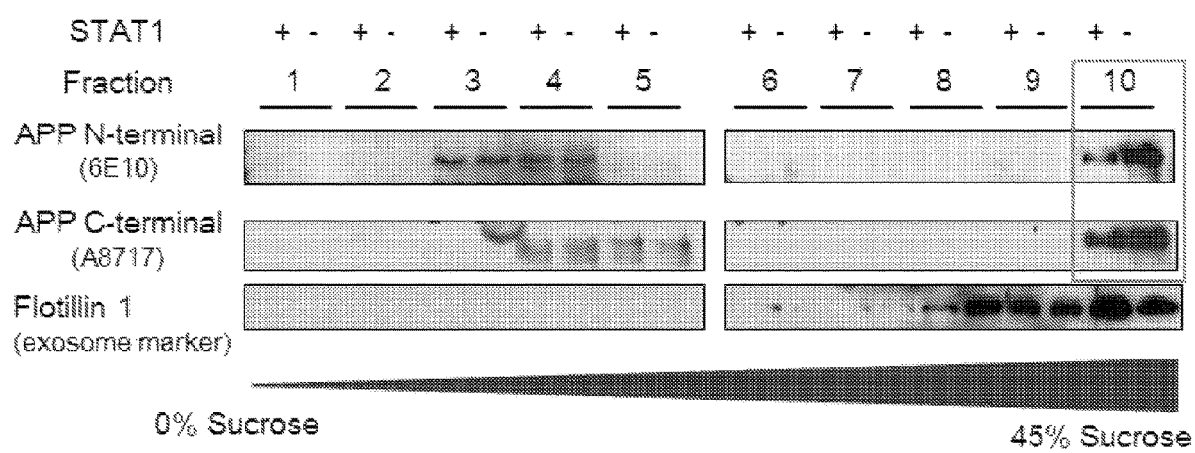
FIG. 7 shows images depicting that full-length APP protein is reduced in exosomal fraction of STAT1−/− mice. Brain tissues from APP/PS1 and APP/PS1/STAT1−/− mice were homogenized, and the post-nuclear fraction was subjected to 5%-45% sucrose gradient centrifugation. Ten fractions were collected and solubilized with Triton-100. The fractions were used for western blot and blotted for APP and the exosome marker Flotillin1.

Mice brain homogenate were fractionated by sucrose gradient to examine cellular localization of APP protein. Briefly, the distribution pattern of APP was similar between 5XFAD and 5XFAD/STAT1−/− mice, except in the faction with highest density, which was enriched for Flotillin1, an exosome marker. STAT1−/− mice had significant higher amount of APP in this fraction (FIG. 7).

Figure 8A:
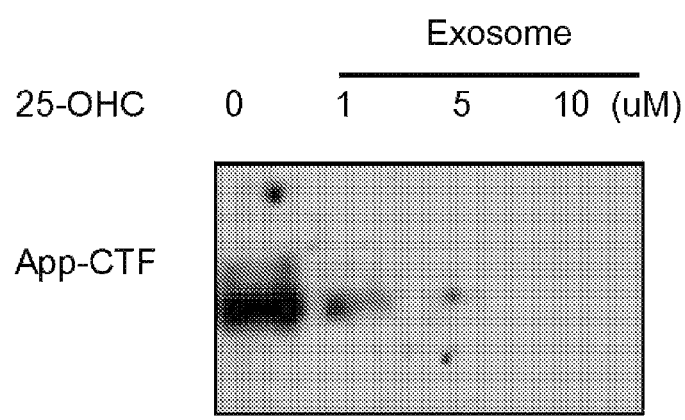
FIGS. 8A-8C show graphs and images depicting that treatment with 25-OHC decreased exosomal APP but increases intracellular APP. SH-SY5Y cells with APP overexpression were treated with different dosage of 25-OHC.
Figure 8B:
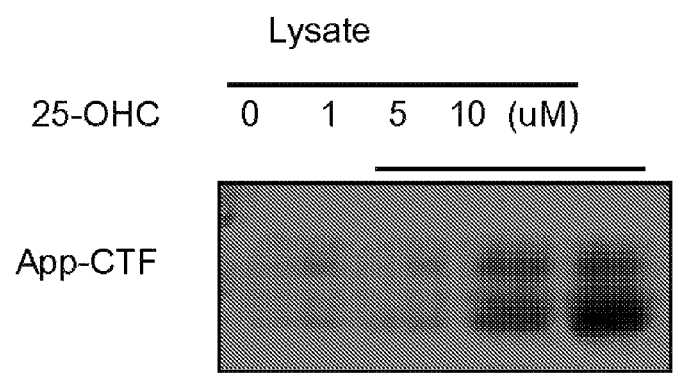

We used APP over-expression SH-SY5Y cell line to further check if the difference in exosomal APP is due to 25-OHC. Cells were treated with different dosage of 25-OHC and both cell lysate and exosomes from medium were collected. 25-OHC showed a dosage dependent effect to increase cellular APP while decreasing exosomal APP (FIGS. 8A and 8B). As shown in FIG. 8A, as the dosage of 25-OHC increased, less APP was found in the Exosome fraction. In contract, as the dosage of 25-OHC increased, more APP was found in the cell lysate fraction.

Figure 8C:
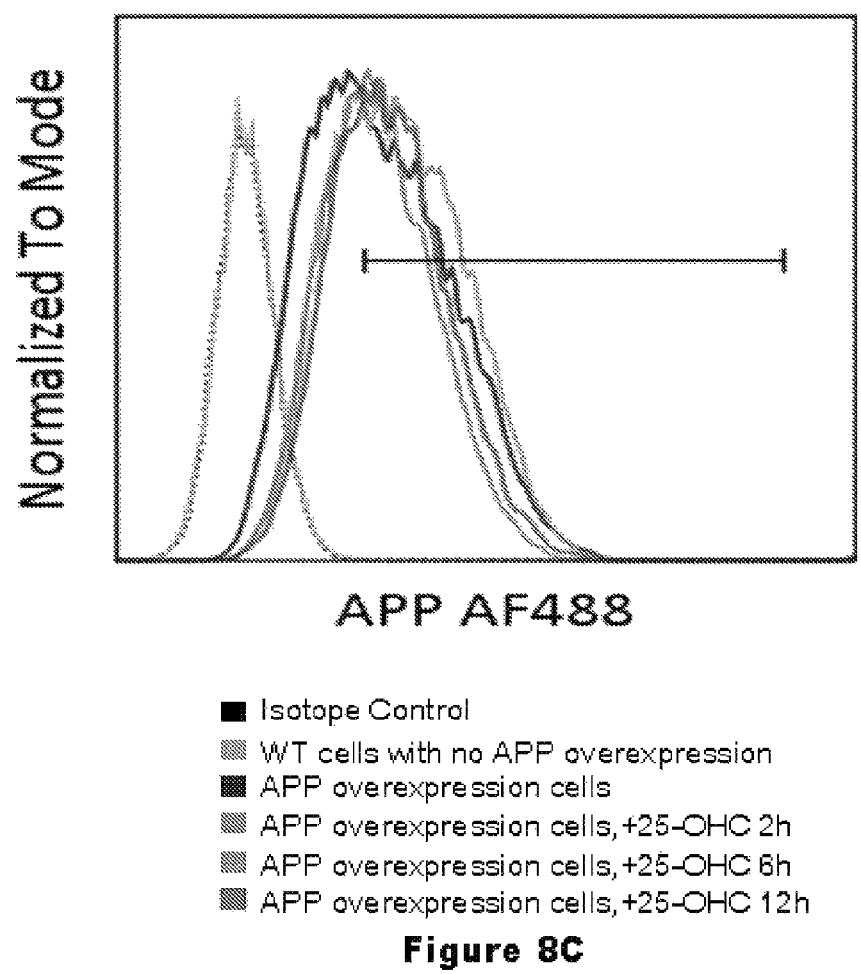

FACS analysis of surface APP also revealed 25-OHC increased the amount of APP on cell surface (FIG. 8C). More amounts of APP were detected on the cell surface of cells overexpressing APP after 25-OHC treatment.

Figure 9:
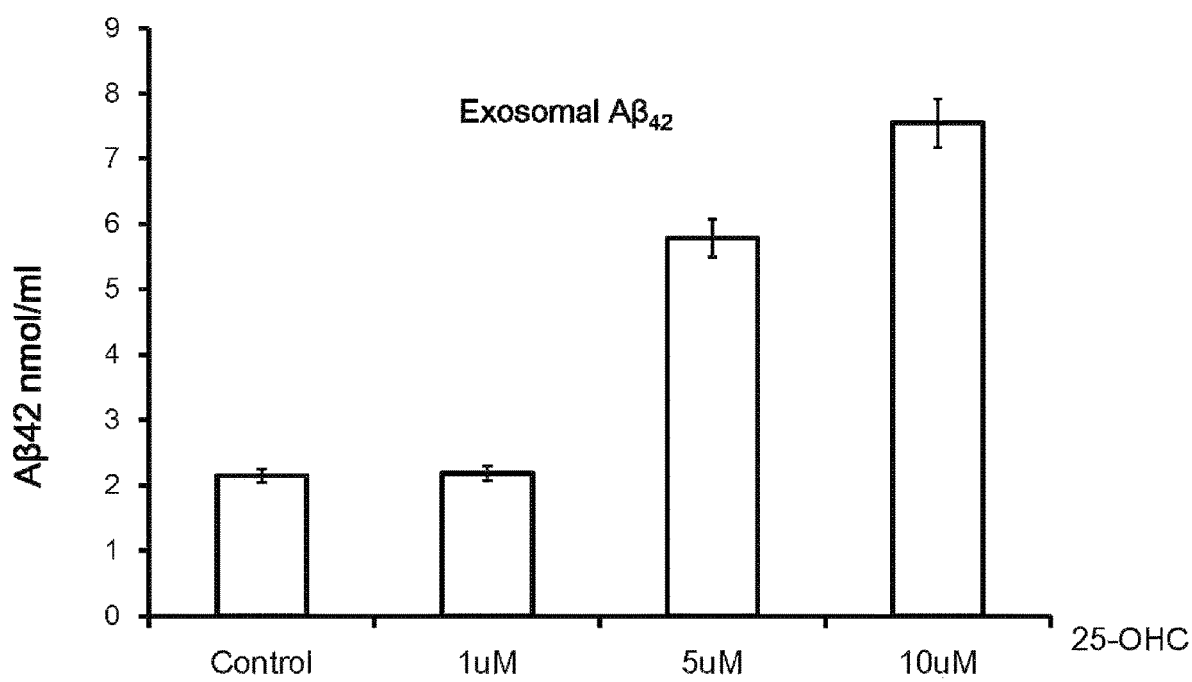
FIG. 9 shows a graph depicting increased Aβ42 in exosomes after treatment with 25-OHC. ELISA measurement of Aβ42 in exosomes collected from cell culture medium with different concentration of 25-OHC treatment. Data are representative of three independent experiments. $*p<0.05$.

Further, we found that increased Aβ42 in exosomes after treatment with 25-OHC. cell culture medium with different concentration of 25-OHC treatment were collected and Aβ42 in exosomes collected from the medium were measured by ELISA. As shown in FIG. 9, increased Aβ42 was detected in medium from cells treated with increased 25-OHC concentration. Data are representative of three independent experiments.

Example 4 25-OHC Increased Retention Time of APP in Cells

Multiple mechanism could contribute to the increase of cellular APP following 25-OHC treatment. However, our mouse data suggested both the synthesis and degradation of APP were normal: the expression of APP was similar, and the enzymes for APP cleavage was also comparable (FIGS. 16A and 16B). As shown in FIG. 16A, the expression level of APP was similar regardless of STAT1 deficiency. As shown in FIG. 16B, the expression level of Adam10, BACE1 and Nicastrin, i.e., the α, β, and γ secretase of APP, respectively were also similar regardless of STAT1 deficiency.

Figure 10A:
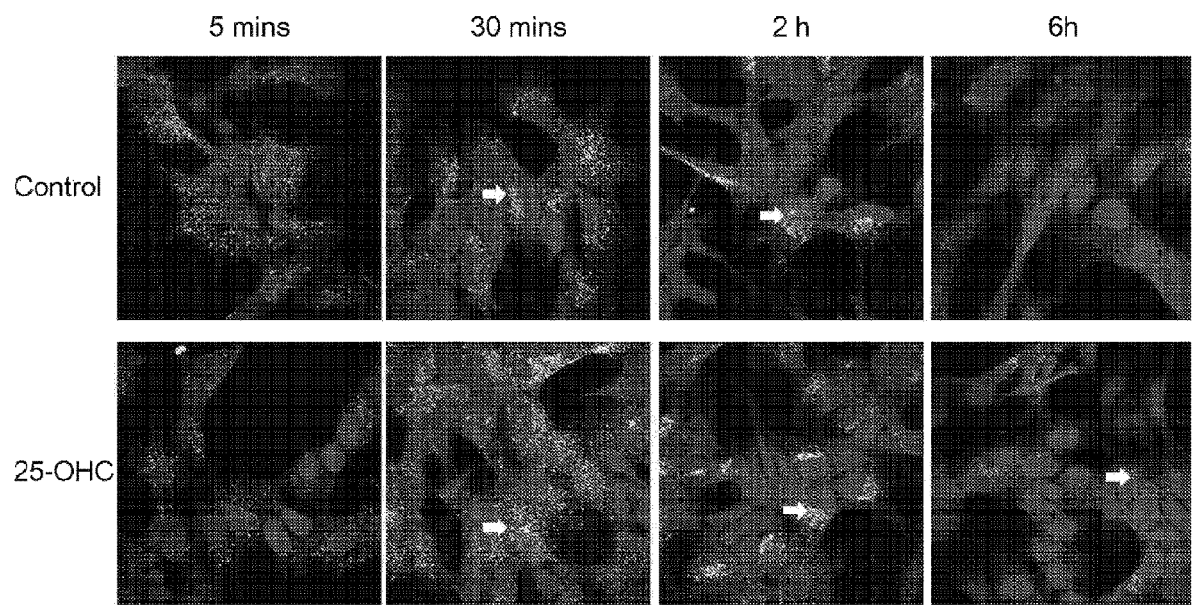
FIGS. 10A-10C show images depicting increased retention time of APP inside cells after treatment with 25-OHC.
Figure 10B:
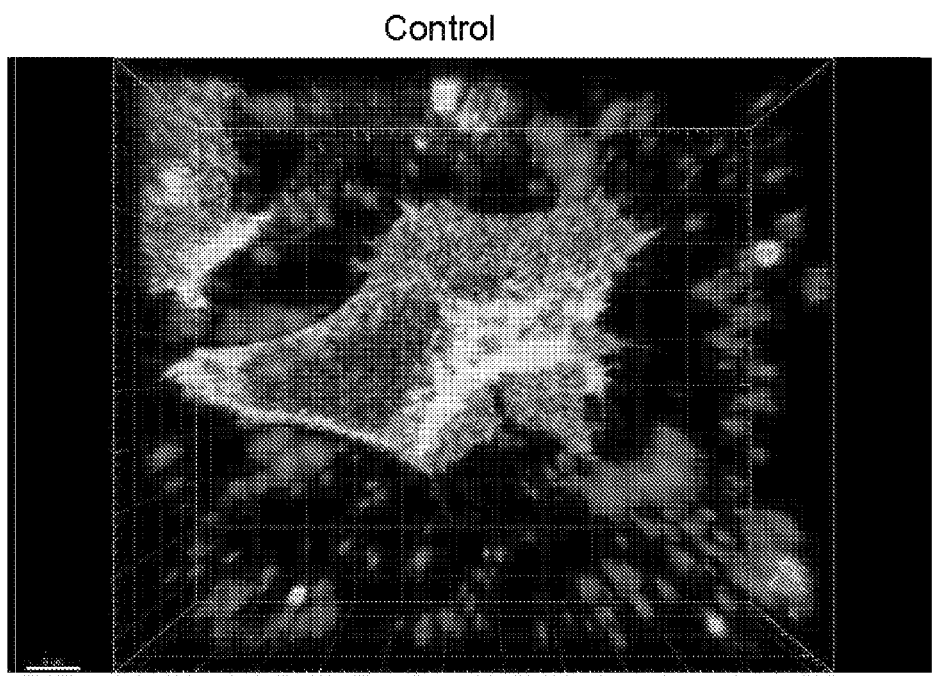
Figure 10C:
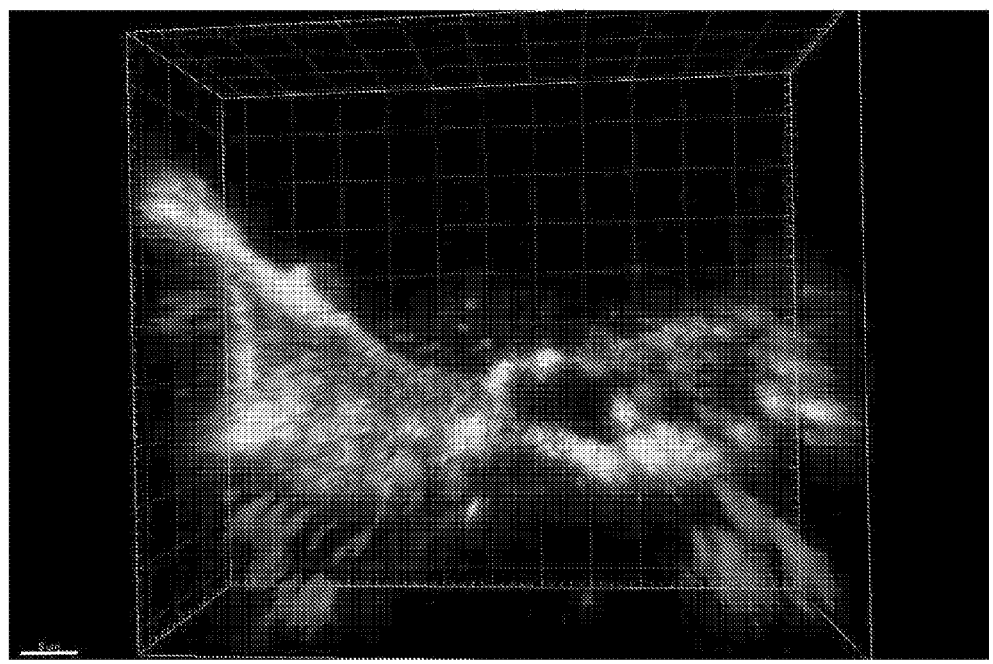

We went on to check the trafficking of APP protein. Surface APP were labeled by antibody, and cells were put back to incubator and fixed at different time point for staining. In untreated cells, APP quickly went to specific compartment in the cell, and within 6 hours, the signal disappeared, while in the 25-OHC treated cells, the trafficking of APP was slower (FIG. 10A). Timelapse movie showed clearly in untreated cells, APP cluster to specific compartment while in 25-OHC treated cells, APP were still evenly distributed within the time of examination (FIG. 10B).

Figure 12D:
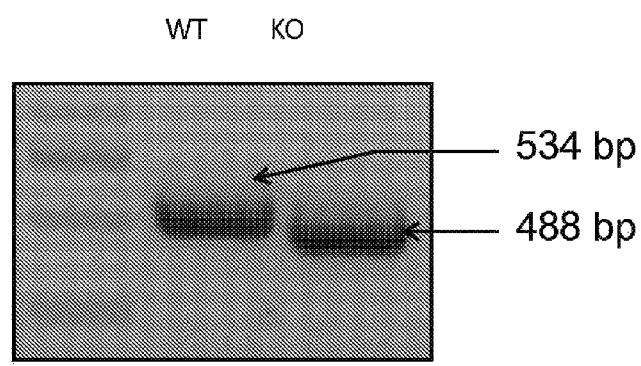

Example 5 CH25H KO Recaptulated the Phenotype of STAT1 KO to Delay AD Pathogenesis We studied the effect of CH25H KO in AD pathogenesis. SgRNAs targeting CH25H were designed with sgRNA1 being SEQ ID NO: 1 and sg RNA2 being SEQ ID NO: 2. See FIGS. 12A and 12B. With the two sg RNAs, CH25H gene were knocked out by crisper/cas9 method so that 46 base pairs (bp) were deleted in the exon of CH25H genes (see FIG. 12C), resulting in CH25H knockout (KO) mice.

Figure 12E:
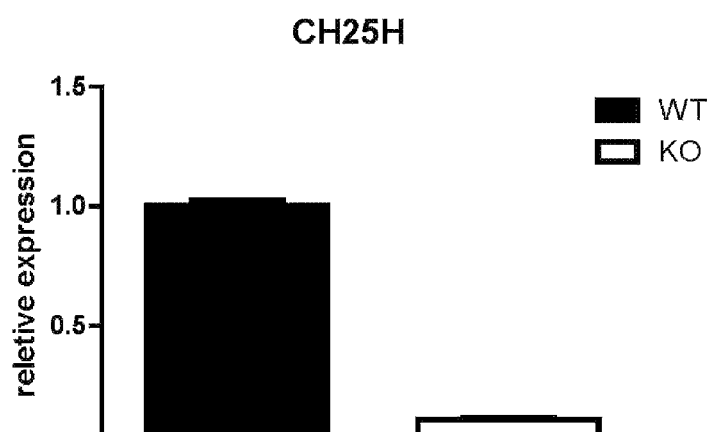

In the CH25H KO mice, the deletion of the 46 bp fragment of CH25H gene was detected with the 488 bp band being the deleted CH25H gene and the 534 bp being the wild-type gene. The expression of CH25H mRNA in the CH25H KO mice was significantly reduced (FIG. 12E).

Figure 11A:
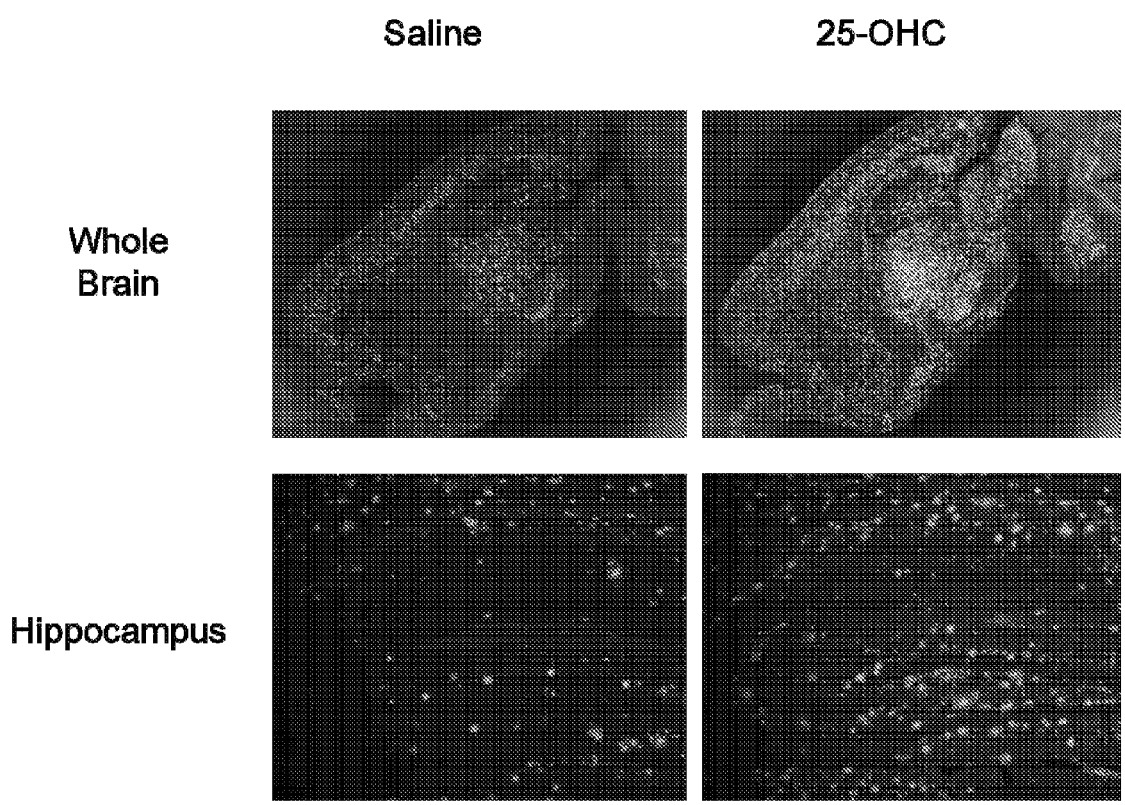
FIGS. 11A, 11B and 11C show images and graphs depicting that injection of 25-OHC promoted Aβ deposition in APP/PS1 mice.
Figure 11B:
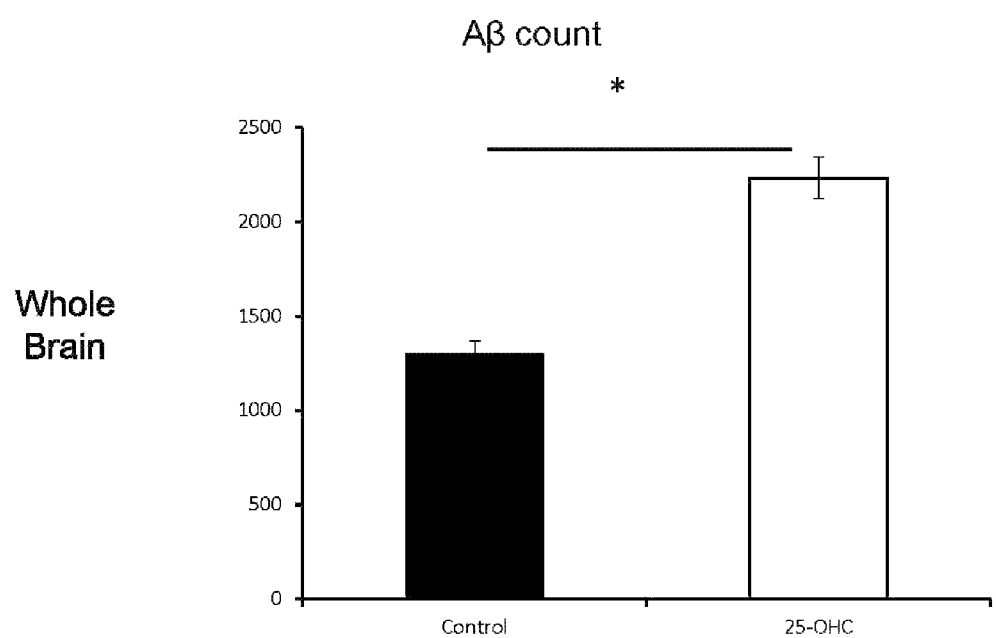
Figure 11C:
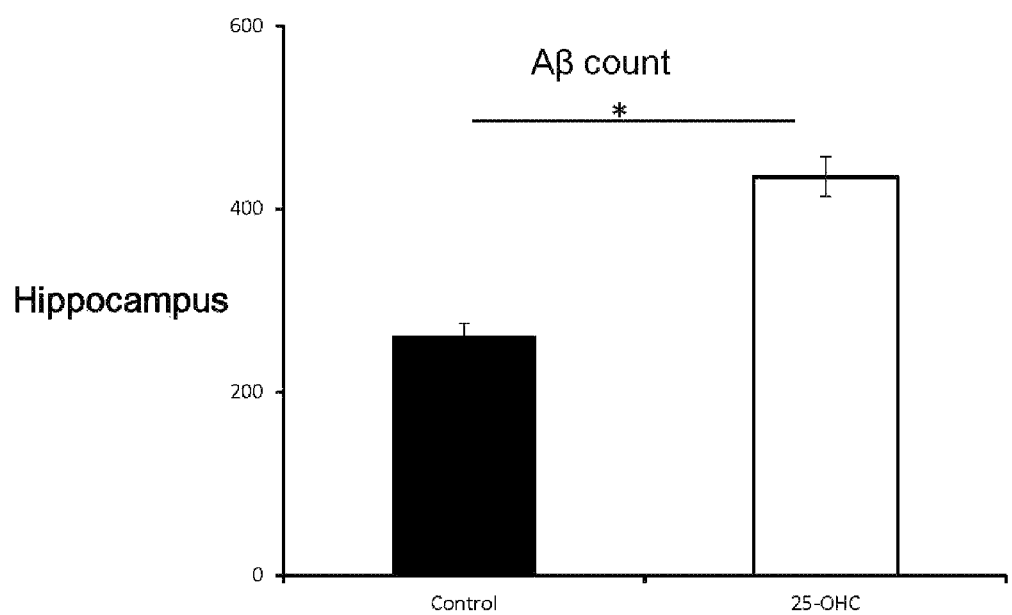
Figure 13A:
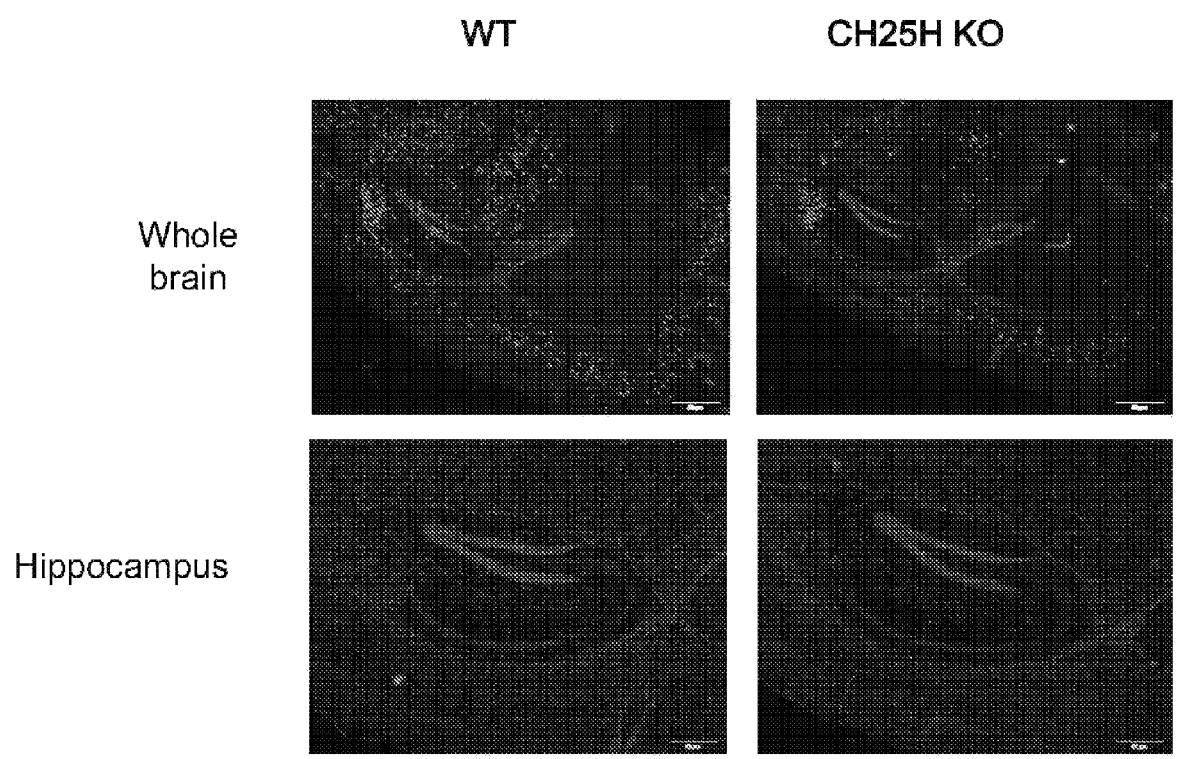
FIGS. 13A and 13B shows images and graphs depicting that Aβ plaque deposition is reduced in CH25H KO mice.
Figure 13B:
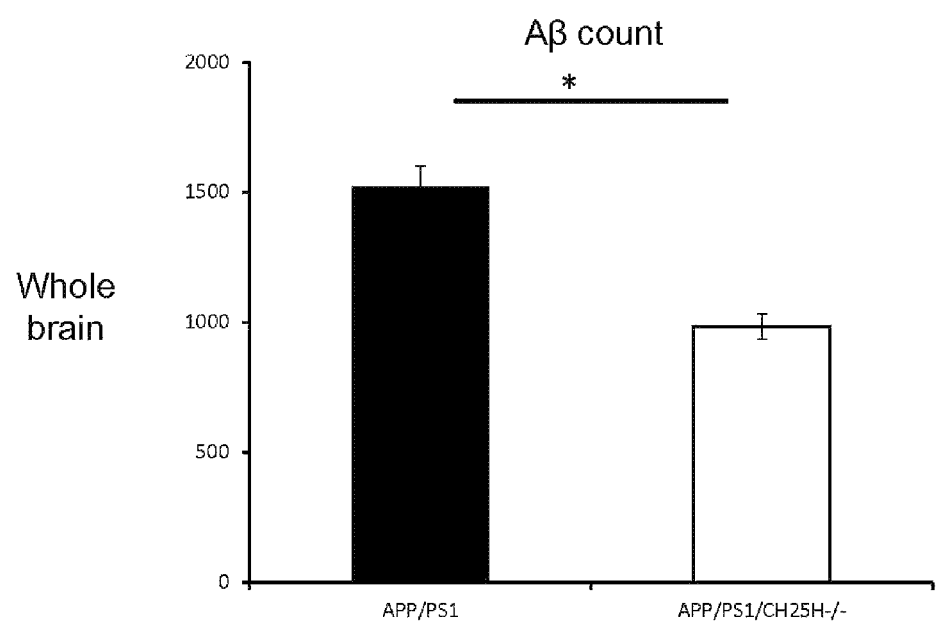
Figure 13C:
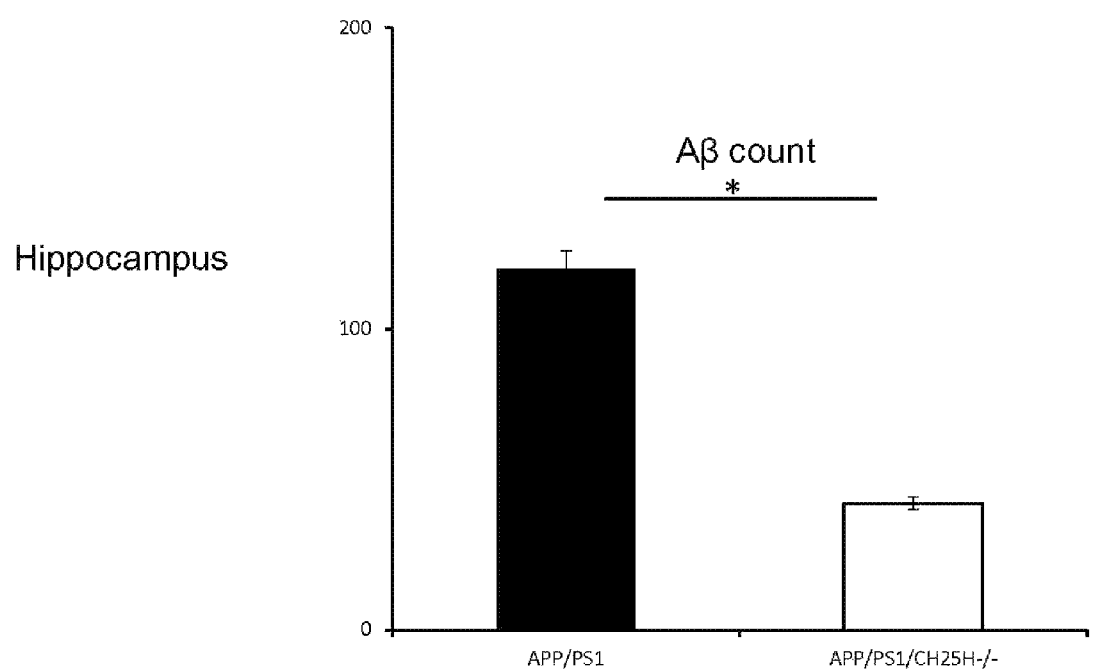

Once crossed to 5XFAD mice, the CH25H KO showed similar phenotype to STAT1 KO. Aβ was greatly reduced in both immunostaining and Elisa quantification (FIGS. 13A, 13B and 13C, respectively). Conversely, mice injected with 25-OHC had significant high amount of Aβ (FIGS. 11A, 11B and 11C).

Figure 14:
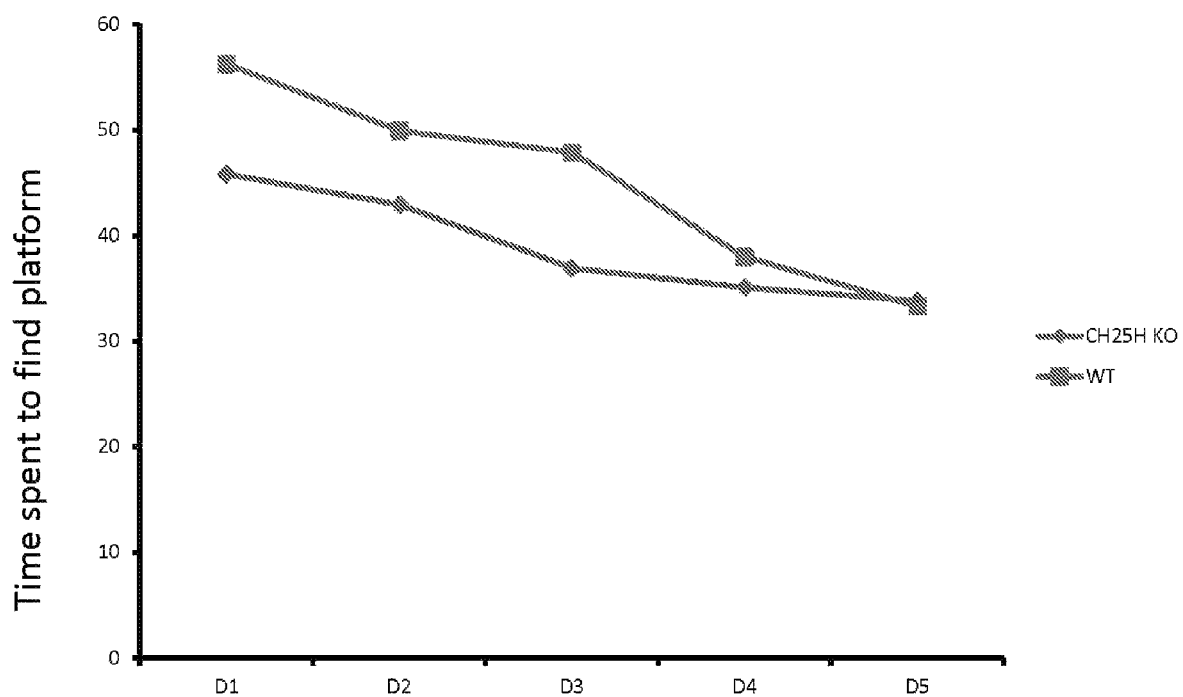
FIG. 14 shows a graph depicting that CH25H gene deficiency improves learning and memory in APP/PS1 mice. APP/PS1 (n=11) and APP/PS/CH25H−/− (n=8) mice were trained for water maze. Average time spent to locate the hidden platform is recorded during 5 days' training. The x-axis is the number of days and the y-axis is the time the mice spent to find platform in the water maze.

To test the effect of reduced Aβ on cognitive abilities, the mice were examined by watermaze. 5XFAD mice gradually learned to locate the platform underneath the water, while the CH25H KO mice took significantly (p<0.05) less time to find the platform, indicating they performed better in learning and memory task (FIG. 14).

Example 6 Simvastatin Inhibits 25-OHC-Induced APP Accumulation

We screened a number of small molecules for potential 25-OHC inhibitor and found that simvastatin blocked 25-OHC induced increase of cellular APP. The effect could be seen with as low as 10 nM of simvastatin, which was much lower than the dosage that could cause cytotoxic effects.

Figure 15:
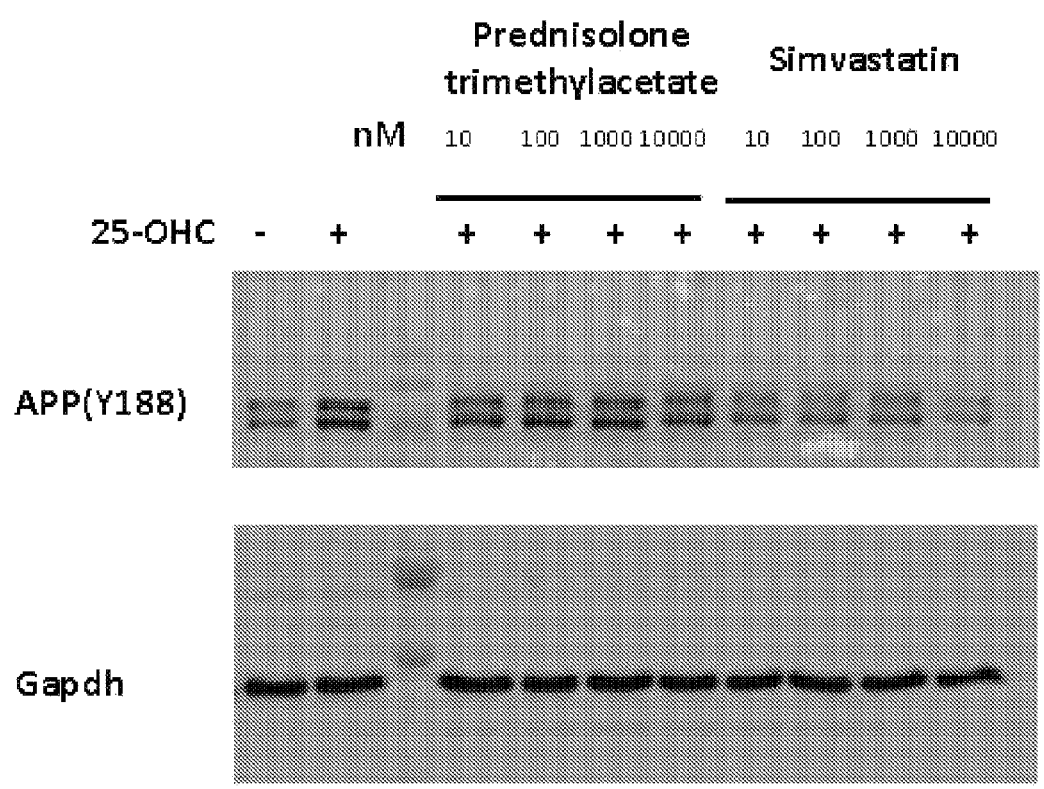
FIG. 15 shows images of Western blots results of APP in cells treated with 25-OHC together with different dosage of Prednisolone trimethylacetate or Simvastatin. Simvastatin acts as a potent 25-OHC inhibitor. SH-SY5Y cells were treated with 25-OHC together with different dosage of Prednisolone trimethylacetate or Simvastatin. Cells were lysed 24 h later and blotted for APP.

As shown in FIG. 15, 25-OHC treatment resulted in increased APP levels. However, simvastatin treatment could reduce the increased APP level induced by 25-OHC treatment. In contrast, prednisolone trimethylacetate treatment had no effect on the increased APP levels induced by 25-OHC. Thus, simvastatin was a potent inhibitor for 25-OHC.

Figure 17A:
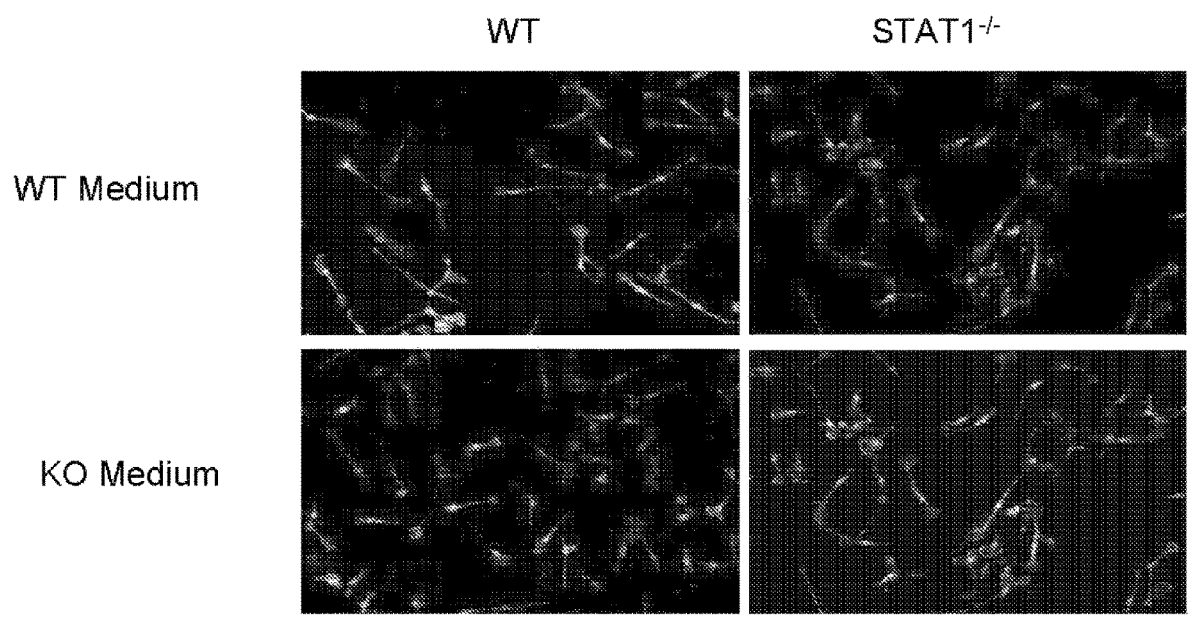
Figure 17B:
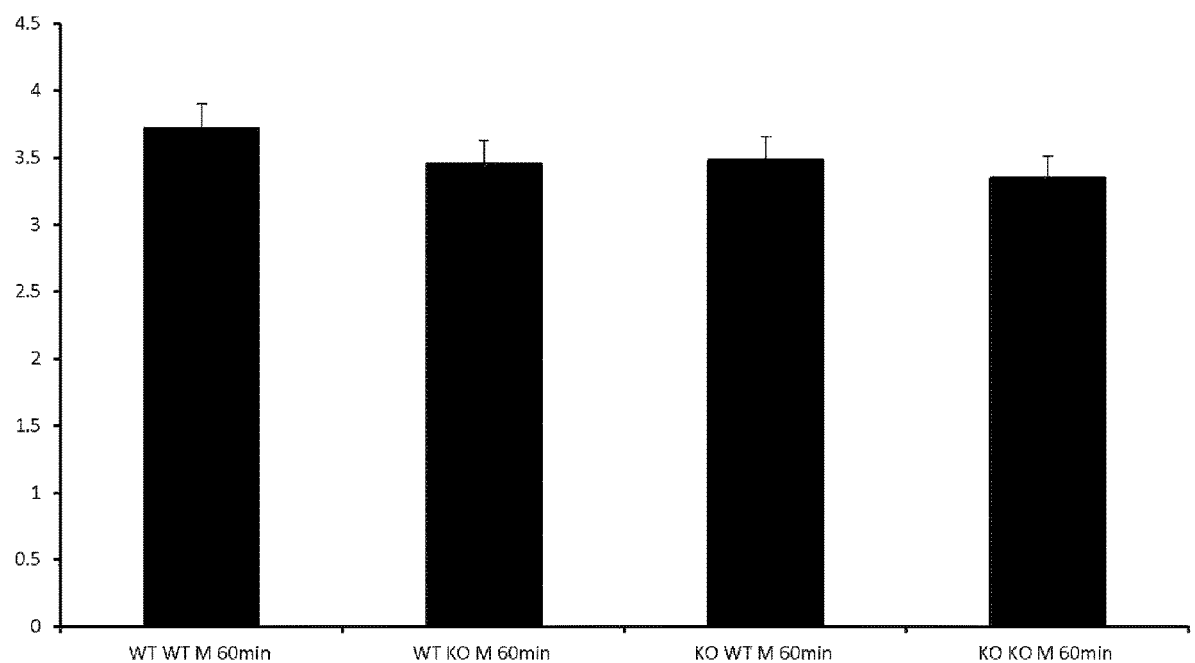
Figure 17C:
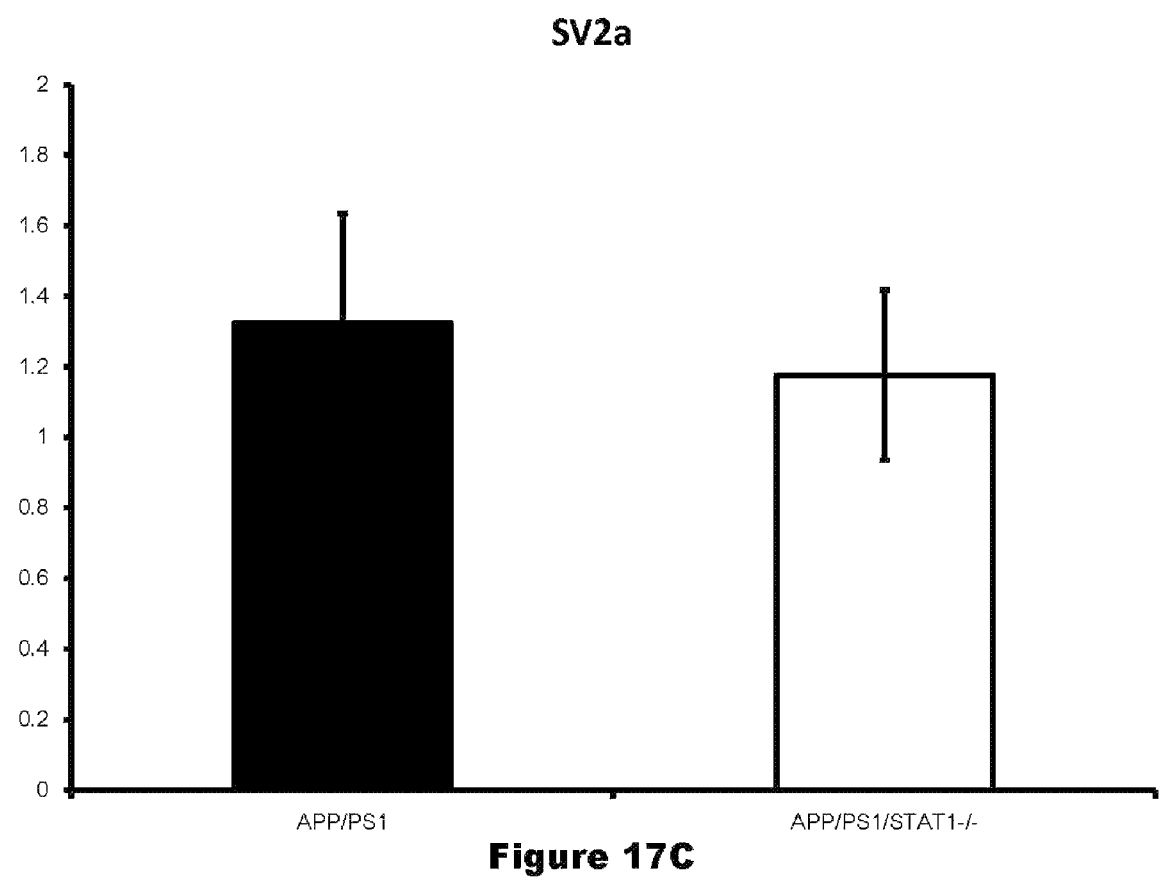
FIG. 17C is a chart depicting real-time PCR measurement of SV2A in WT and STAT1 deficient mice.
Figure 17D:
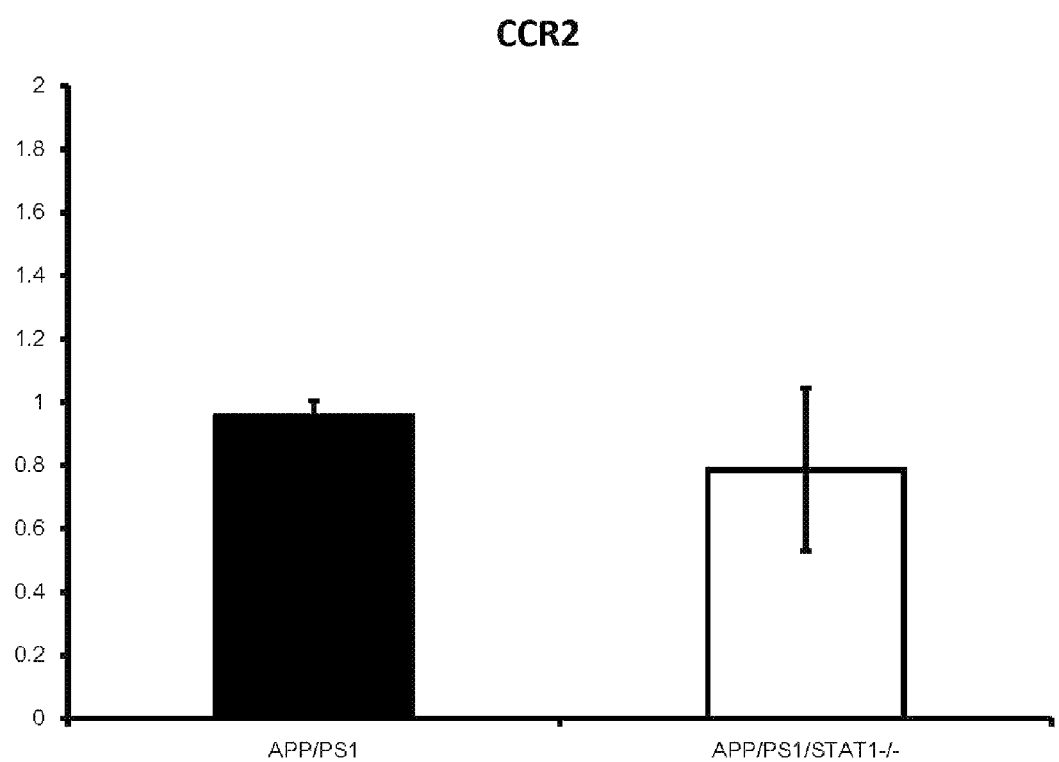
FIG. 17D is a chart depicting real-time PCR measurement of CCR2 in WT and STAT1 deficient mice.
Figure 18A:
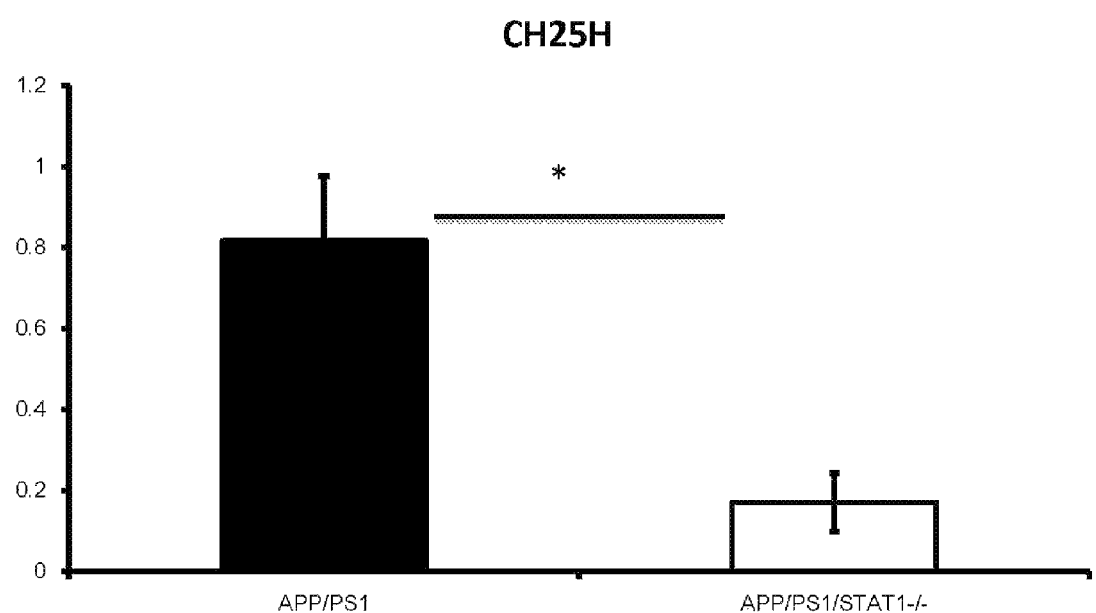
FIGS. 18A, 18B, 18C and 18D show four graphs depicting results of real-time PCR quantification of CH25H (FIG. 18A) and other known cholesterol hydroxylase Cyp46a1 (FIG. 18B), Cyp7b1(FIG. 18C) and Cyp7a1(FIG. 18D) in brain tissues of APP/PS1 and APP/PS1/STAT1−/− mice, respectively. The results show that other cholesterol hydroxylases Cyp46a1, Cyp7b1 and Cyp7a1 were not affected by STAT1 deficiency.
Figure 18B:
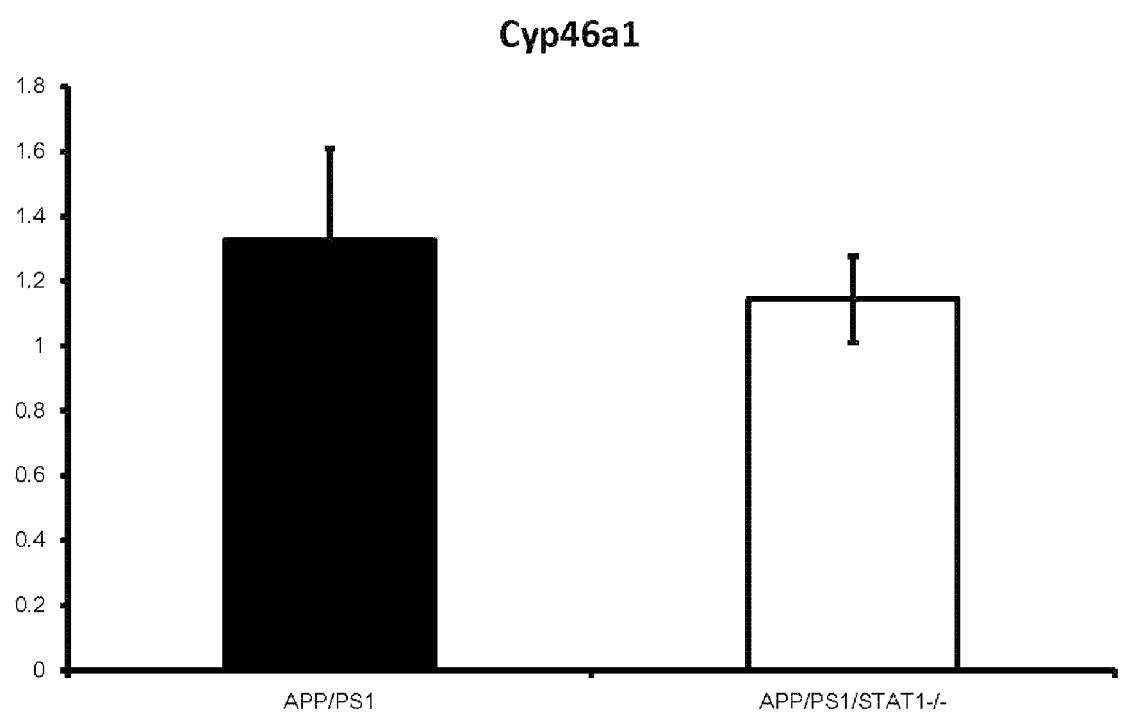
Figure 18C:
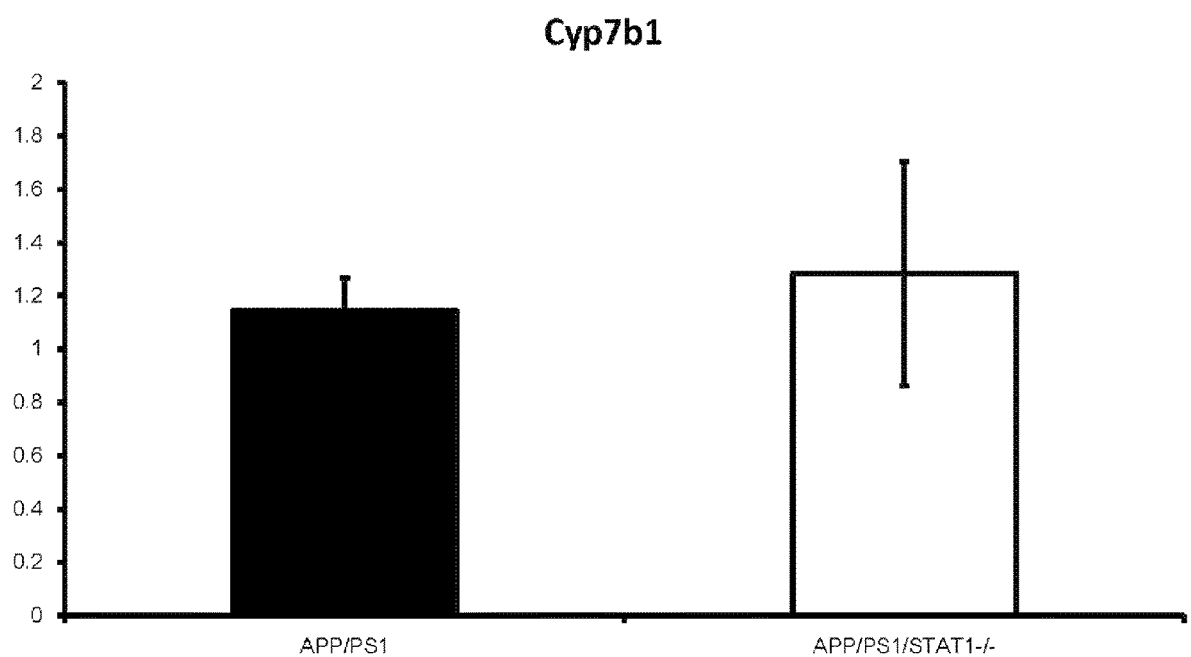
Figure 18D:
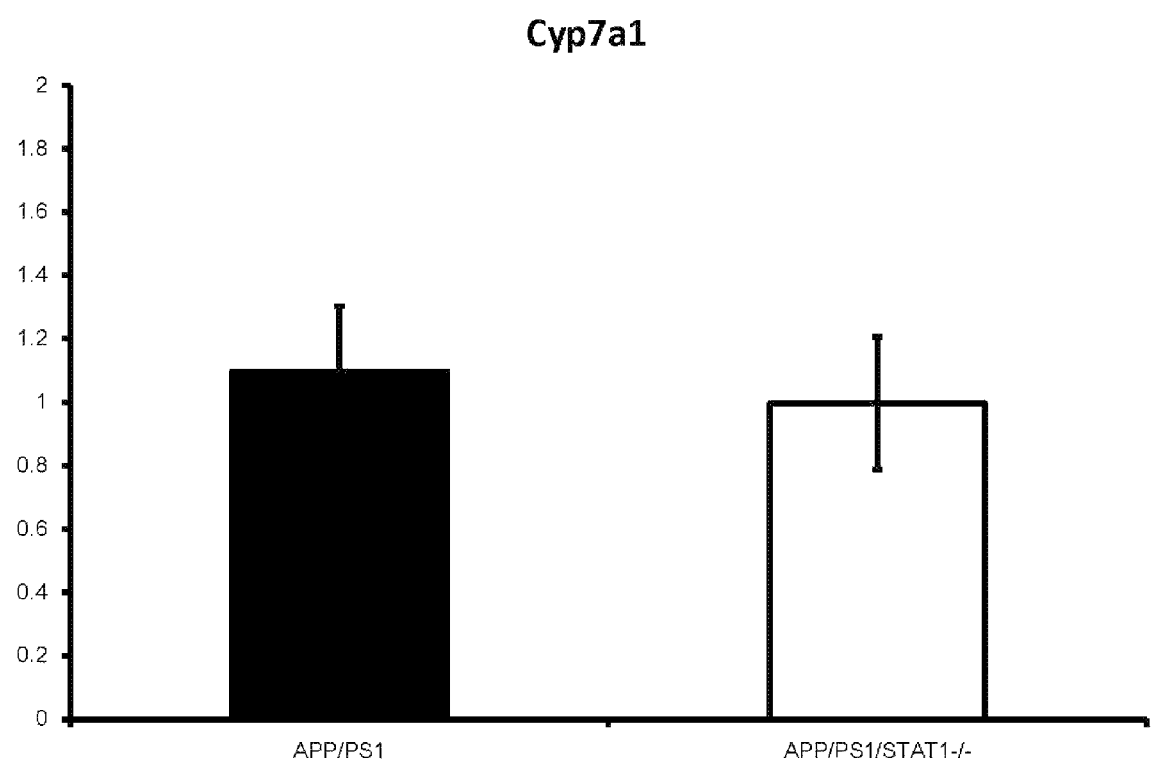

Example 7 Phagocytosis Between WT and STAT1 Deficient Microglia Cells were Similar WT or STAT1-/- microglia cells were incubated with fluorescent beads to test their phagocytotic ability. To examine the effect of secreted factors in medium, both cells were kept in medium from WT cells or in medium from STAT1-/- cells. Imaging and quantification showed phagocytosis was similar in all conditions tested (FIGS. 17A and 17B). We also measured mRNA of SV2a and CCR2, key genes involved in phagocytosis process. Their expression levels were similar between APP/PS1 and APP/PS1/STAT1-/- (FIG. 17C and FIG. 17D).

Example 8 CH25H was STAT1 Dependent Cholesterol Hydroxylase

We tested several known cholesterol hydroxylase, including CH25H, Cyp46a1, Cyp7b1 and Cyp7a1, that added hydroxy group to cholesterol at different positions. Among the enzymes we tested, only CH25H showed STAT1 dependent expression pattern as only the expression of CH25H was decreased significantly (FIGS. 18A, 18B, 18C and 18D).

Example 9 STAT1 Deficiency Did not Cause General Metabolic Defect

Figure 19A:
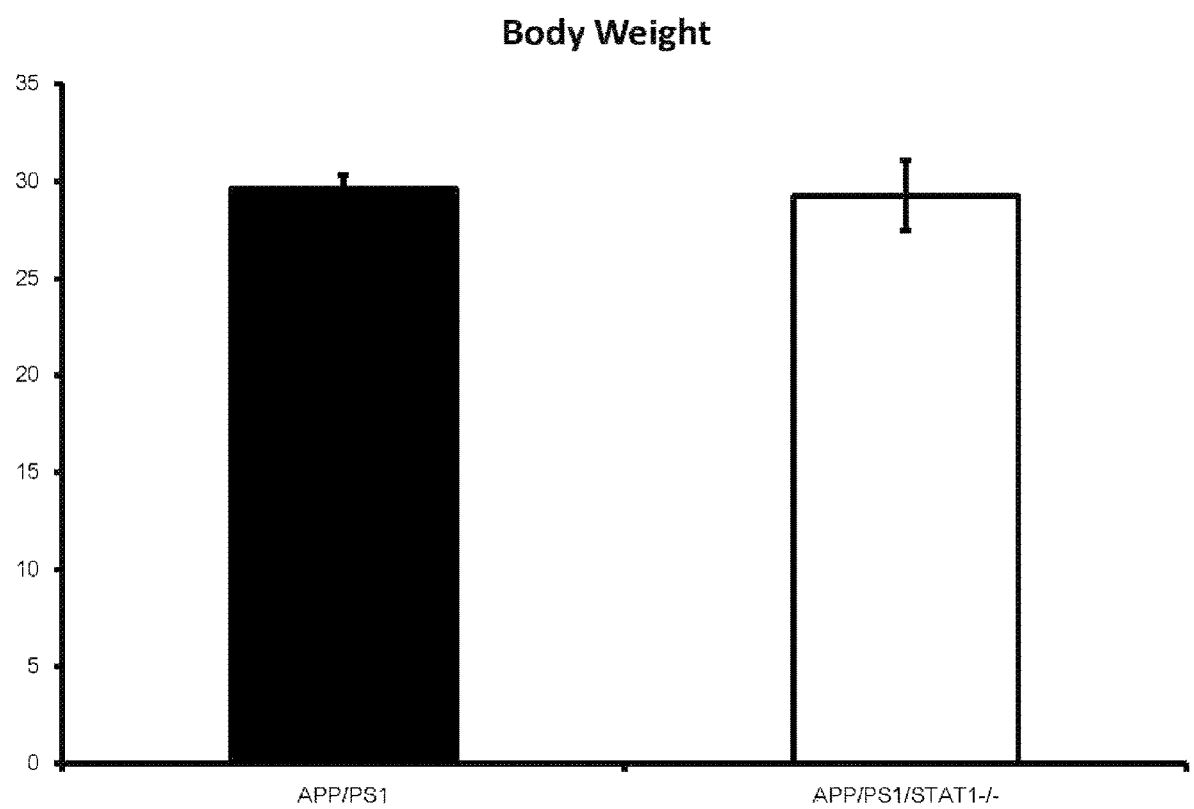
FIGS. 19A-19F show graphs and images depicting that STAT1 deficiency did not affect general lipid metabolism.
Figure 19B:
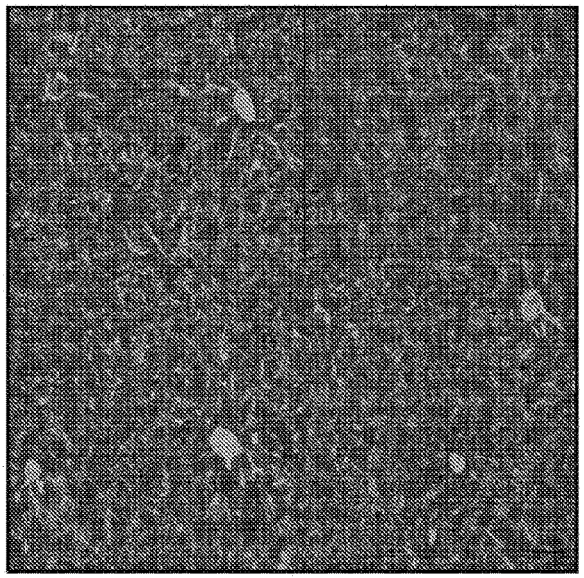
Figure 19B:
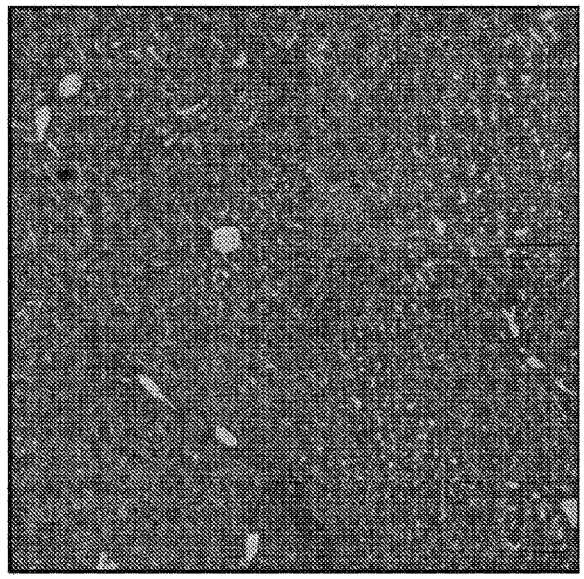
Figure 19C:
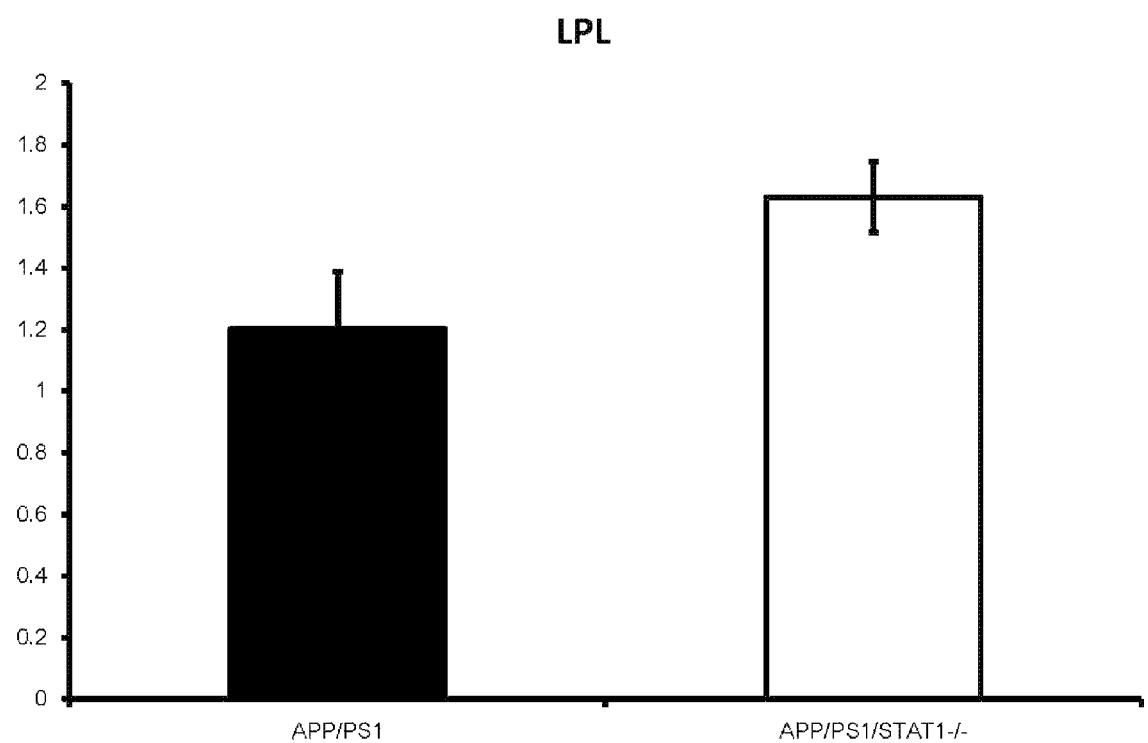
Figure 19D:
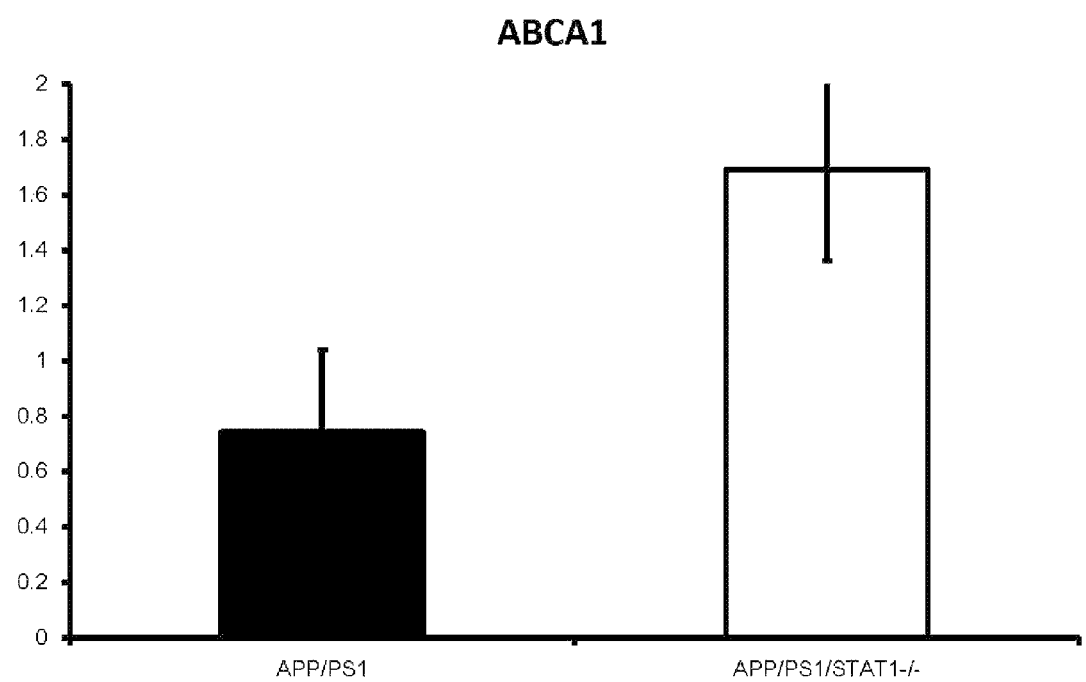
Figure 19E:
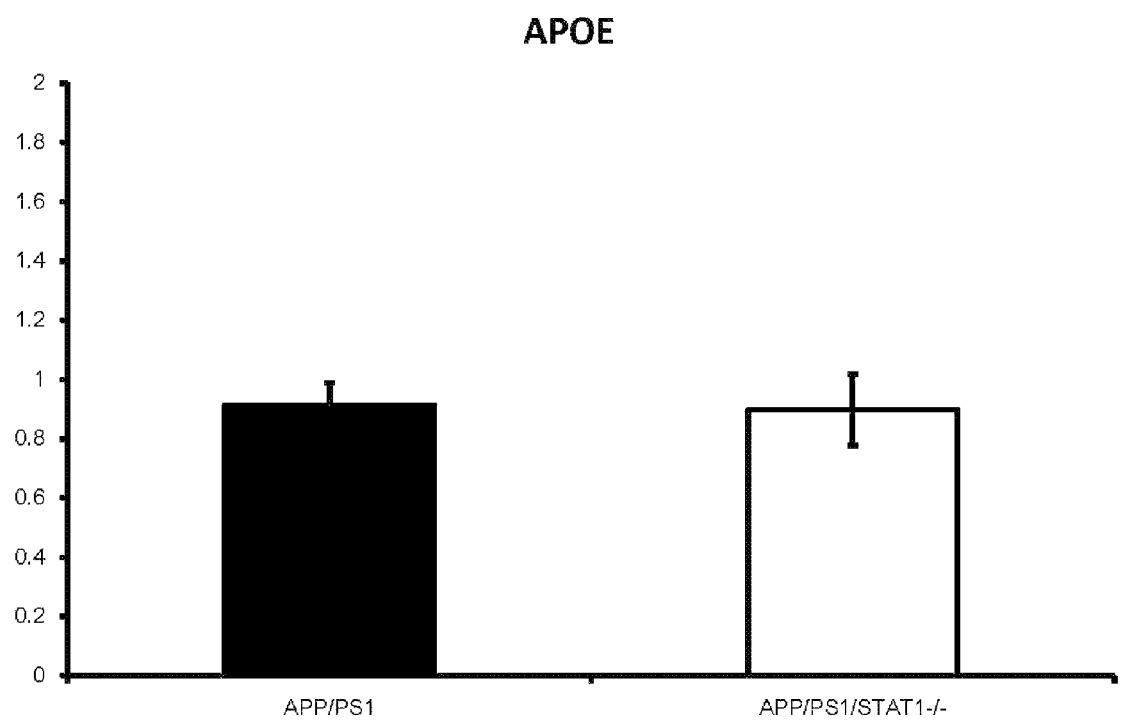
Figure 19F:
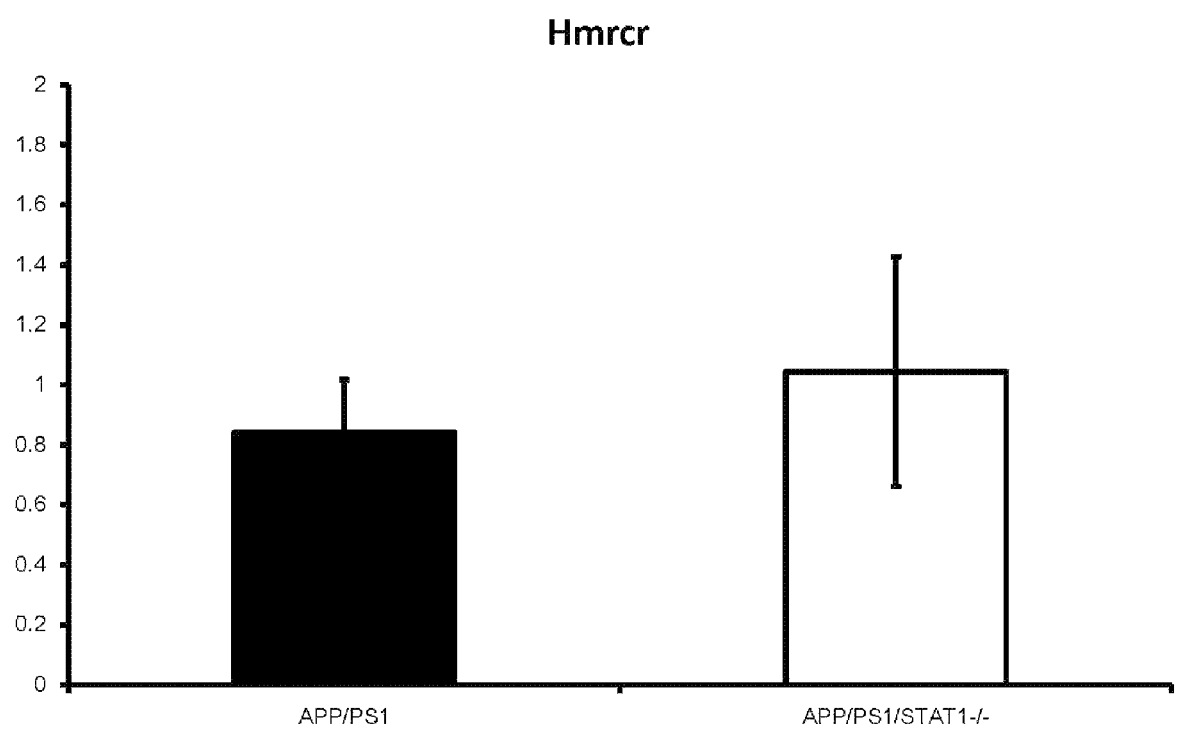
Figure 20A:
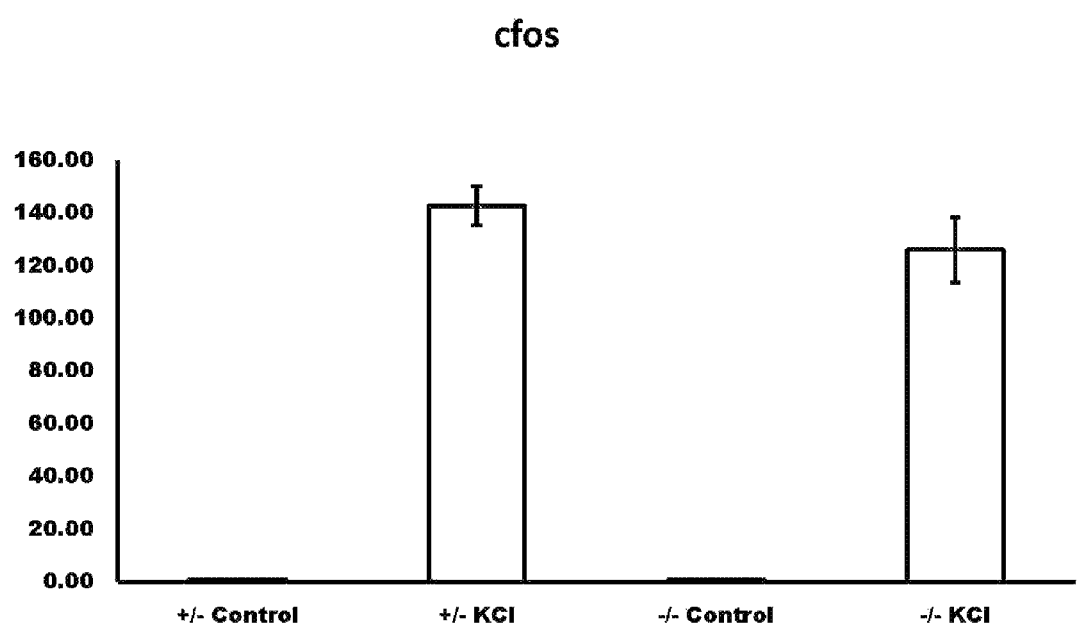
FIGS. 20A, 20B, 20C, 20D, 20E, 20F, and 20G show graphs depicting results of real-time PCR quantification of c-fos (FIG. 20A), zif268 (FIG. 20B), BDNF-IV (FIG. 20C), BDNF-IX (FIG. 20D), Gadd45b (FIG. 20E), Npas4 (FIG. 20F) and CH25H (FIG. 20G) in primary neuron culture obtained from WT or STAT1 KO mice after treatment with 50 mM of KCl for 30 mins to measure the induction of immediate early genes after KCl treatment. The results show that STAT1 deficiency did not change basal neural activity.
Figure 20B:
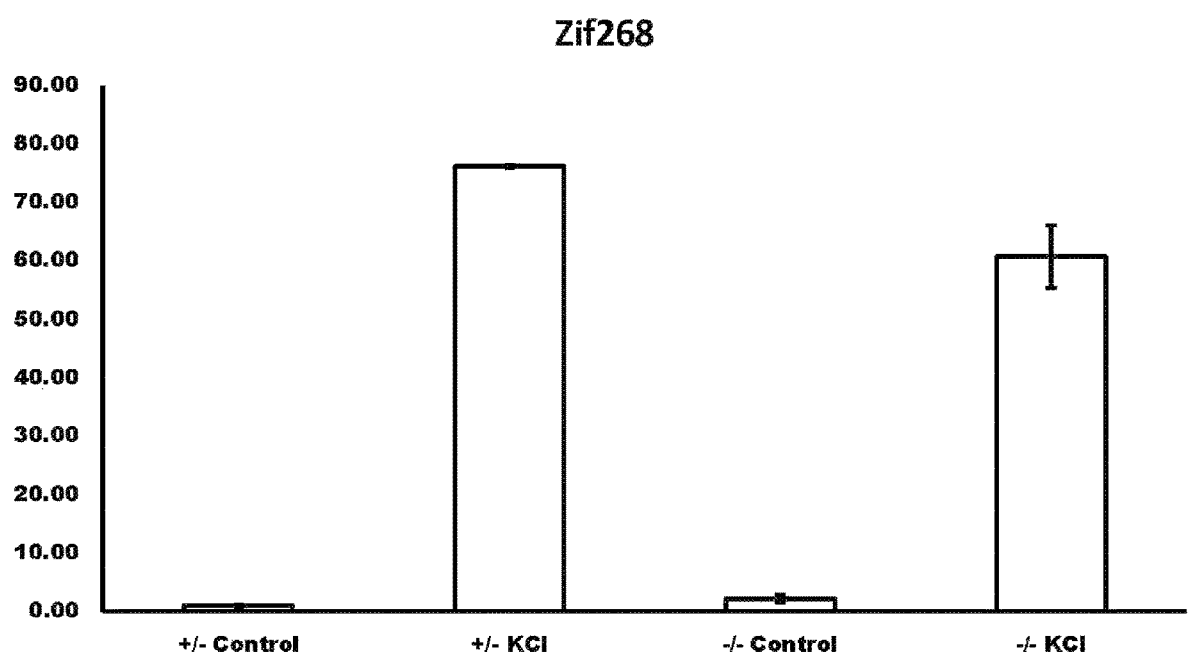
Figure 20C:
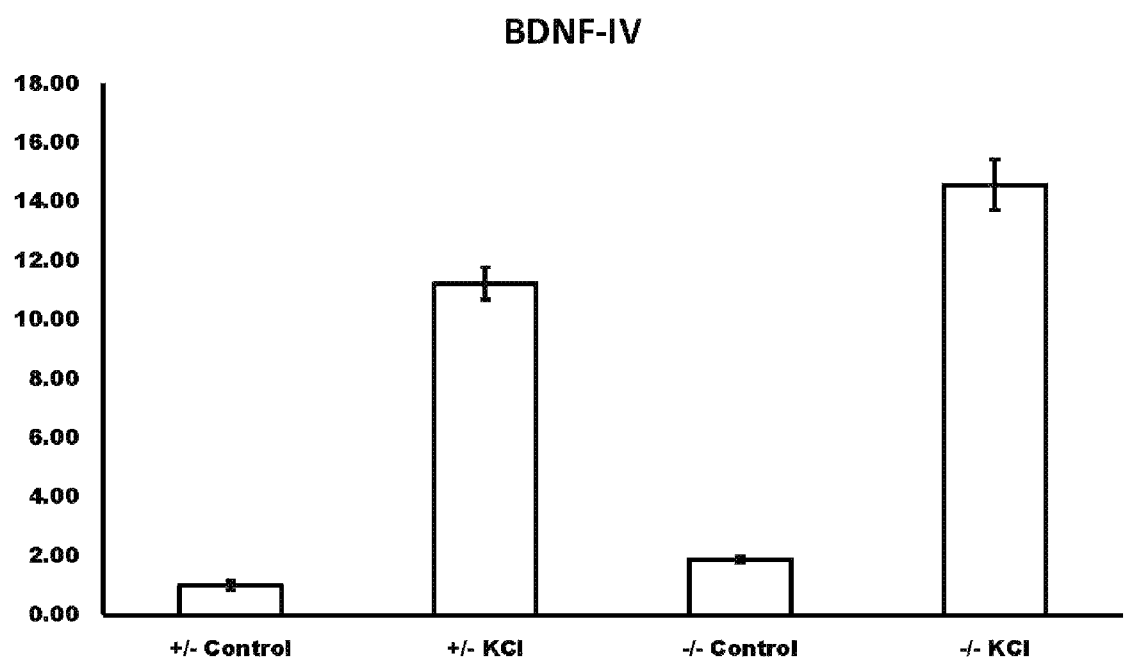
Figure 20D:
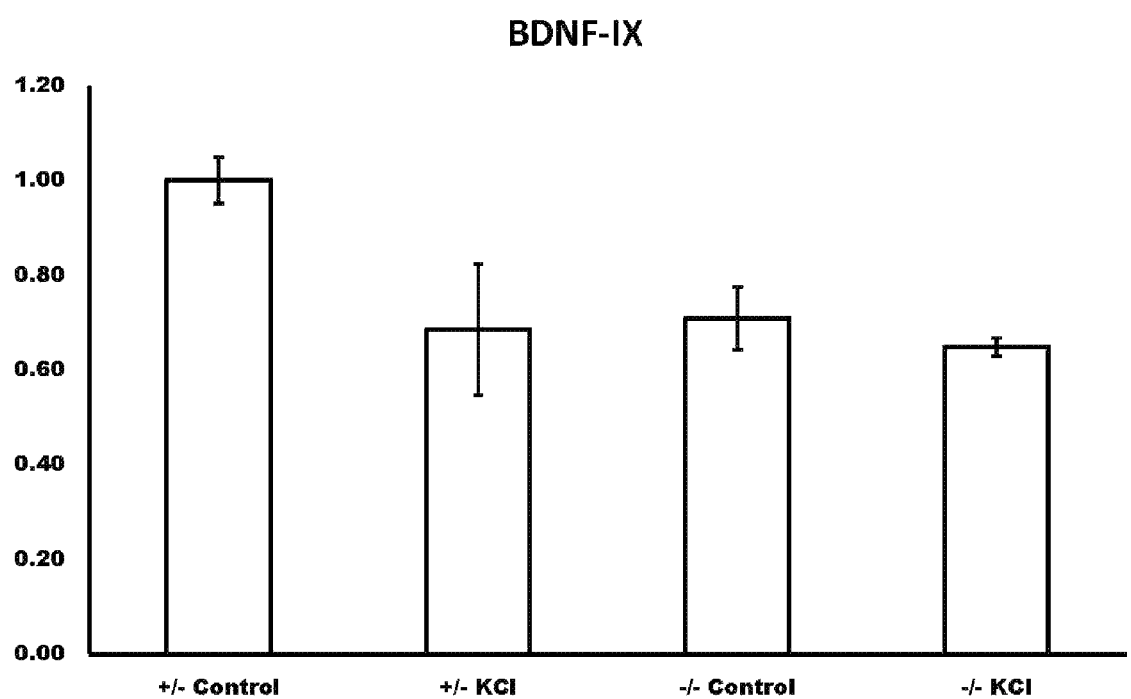
Figure 20E:
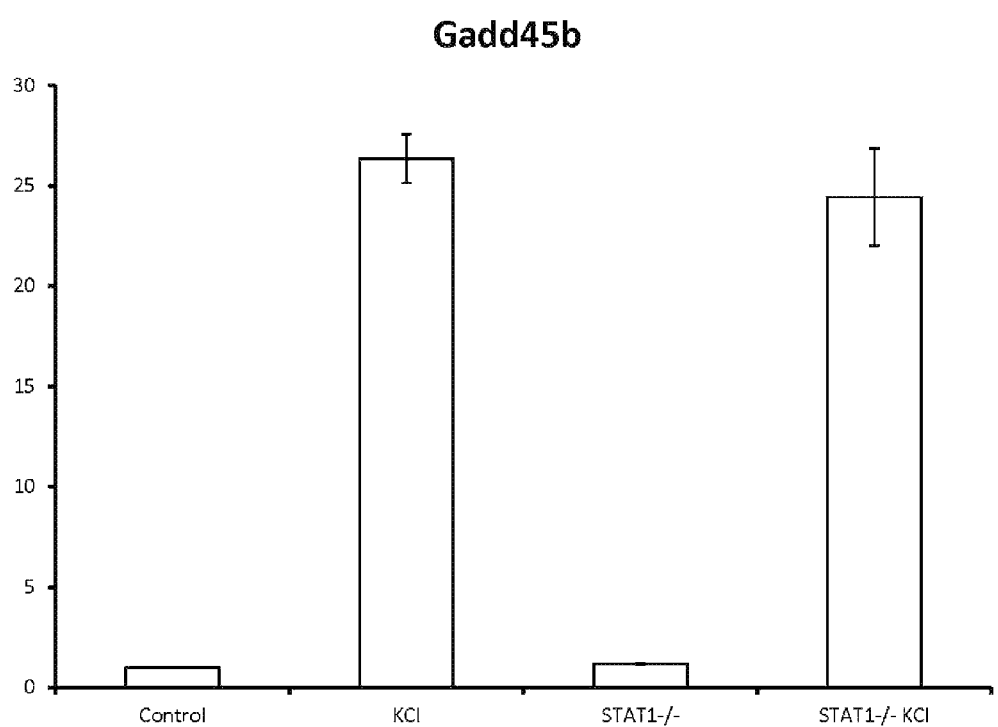
Figure 20F:
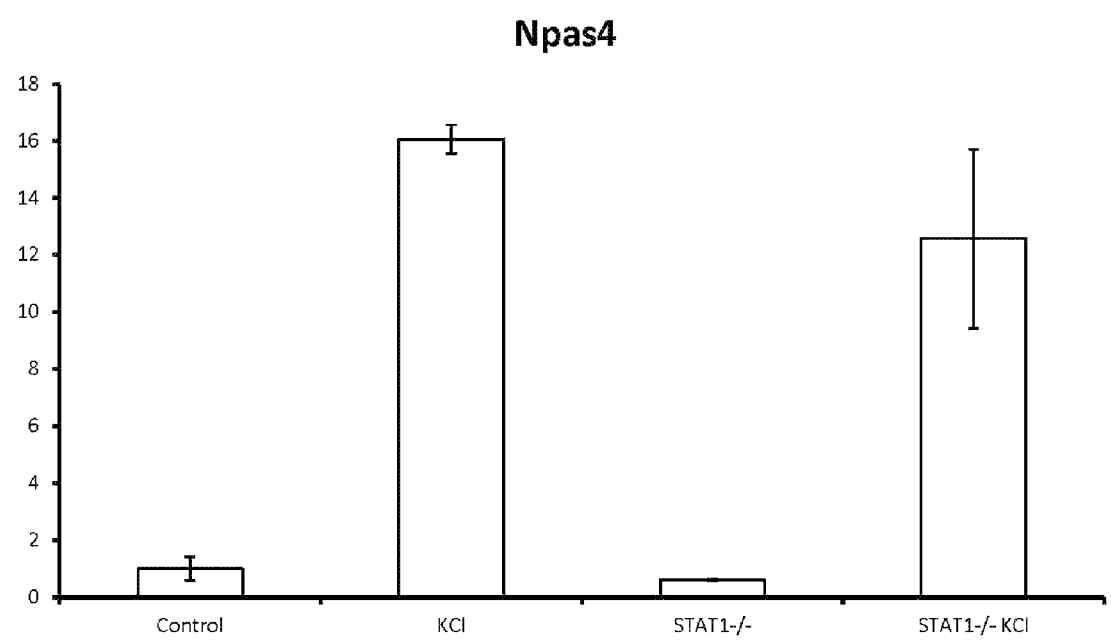
Figure 20G:
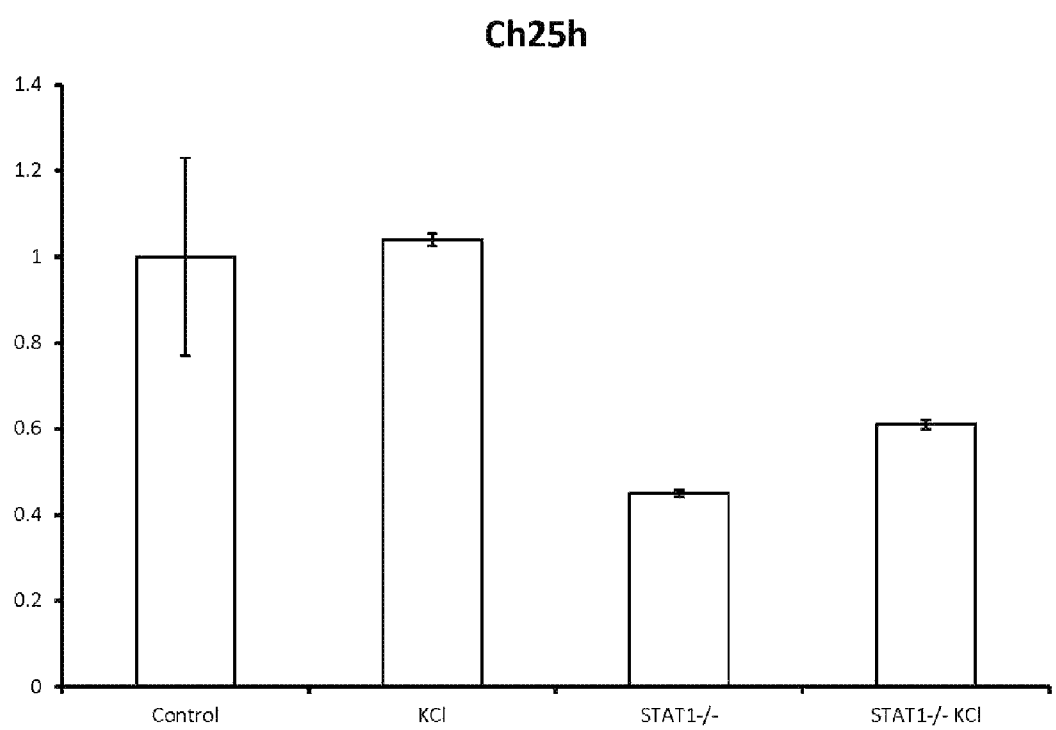

CH25H was originally known to regulate cholesterol metabolism. However, when we compared the body weight, lipid deposition in liver and key enzymes involved in lipid metabolism, there was no significant change between WT and STAT1-/- mice (FIGS. 19A-19F). As shown in FIG. 19A, there was no significant difference of the body weight between APP/PS1 and APP/PS1/STAT1-/- mice. As shown in FIG. 19B, there was no significant difference in lipid deposition in liver cells between APP/PS1 and APP/PS1/STAT1-/- mice. Further, as shown in FIGS. 19C-19F, there were no significant difference of the expression of key enzymes including LPL, ABCA1, APOE, HMGCR between APP/PS1 and APP/PS1/STAT1-/- mice.

Example 10 STAT1 Deficiency Did not Alter Neuronal Activity Measured by Induction of Immediate Early Genes Primary hippocampal neurons from WT or STAT1-/- mice were cultured and then treated with 50 mM KCl. Induction of some of the immediate early genes including cfos, Zif268, BDNF-IV, BDNF-IX, Gadd45b, Npas4 and Ch25 h, were measured by RT-PCR as markers for neuronal activity. As shown in FIGS. 20A-20G, both WT and STAT1-/- neurons were capable to induce these genes, to a similar extent.

REFERENCE

Bonni, A., Y. Sun, M. Nadal-Vicens, A. Bhatt, D. A. Frank, I. Rozovsky, N. Stahl, G. D. Yancopoulos and M. E. Greenberg (1997). "Regulation of gliogenesis in the central nervous system by the JAK-STAT signaling pathway." *Science* 278(5337): 477-483.

Chen, Y. C., W. L. Hsu, Y. L. Ma, D. J. Tai and E. H. Lee (2014). "CREB SUMOylation by the E3 ligase PIAS1 enhances spatial memory." *J Neurosci* 34(29): 9574-9589.

Citron, M. (2010). "Alzheimer's disease: strategies for disease modification." *Nat Rev Drug Discov* 9(5): 387-398.

De Strooper, B., R. Vassar and T. Golde (2010). "The secretases: enzymes with therapeutic potential in Alzheimer disease." *Nat Rev Neurol* 6(2): 99-107.

Delrieu, J., P. J. Ousset, T. Voisin and B. Vellas (2014). "Amyloid beta peptide immunotherapy in Alzheimer disease." *Rev Neurol (Paris)* 170(12): 739-748.

Do, D. V., J. Ueda, D. M. Messerschmidt, C. Lorthongpanich, Y. Zhou, B. Feng, G. Guo, P. J. Lin, M. Z. Hossain, W. Zhang, A. Moh, Q. Wu, P. Robson, H. H. Ng, L. Poellinger, B. B. Knowles, D. Solter and X. Y. Fu (2013). "A genetic and developmental pathway from STAT3 to the OCT4-NANOG circuit is essential for maintenance of ICM lineages in vivo." *Genes Dev* 27(12): 1378-1390.

Doody, R. S., R. G. Thomas, M. Farlow, T. Iwatsubo, B. Vellas, S. Joffe, K. Kieburtz, R. Raman, X. Sun, P. S. Aisen, E. Siemers, H. Liu-Seifert, R. Mohs, C. Alzheimer's Disease Cooperative Study Steering and G. Solanezumab Study (2014). "Phase 3 trials of solanezumab for mild-to-moderate Alzheimer's disease." *N Engl J Med* 370(4): 311-321.

Engelhart, M. J., M. I. Geerlings, J. Meijer, A. Kiliaan, A. Ruitenberg, J. C. van Swieten, T. Stijnen, A. Ho man, J. C. Witteman and M. M. Breteler (2004). "Inflammatory proteins in plasma and the risk of dementia: the rotterdam study." *Arch Neurol* 61(5): 668-672.

Etminan, M., S. Gill and A. Samii (2003). "Effect of non-steroidal anti-inflammatory drugs on risk of Alzheimer's disease: systematic review and meta-analysis of observational studies." *BMJ* 327(7407): 128.

Gao, Q., M. J. Wolfgang, S. Neschen, K. Morino, T. L. Horvath, G. I. Shulman and X. Y. Fu (2004). "Disruption of neural signal transducer and activator of transcription 3 causes obesity, diabetes, infertility, and thermal dysregulation." *Proc Natl Acad Sci USA* 101(13): 4661-4666.

Green, R. C., L. S. Schneider, D. A. Amato, A. P. Beelen, G. Wilcock, E. A. Swabb, K. H. Zavitz and G. Tarenflurbil Phase 3 Study (2009). "Effect of tarenflurbil on cognitive decline and activities of daily living in patients with mild Alzheimer disease: a randomized controlled trial." *JAMA* 302(23): 2557-2564.

Heneka, M. T., M. P. Kummer, A. Stutz, A. Delekate, S. Schwartz, A. Vieira-Saecker, A. Griep, D. Axt, A. Remus, T. C. Tzeng, E. Gelpi, A. Halle, M. Korte, E. Latz and D. T. Golenbock (2013). "NLRP3 is activated in Alzheimer's disease and contributes to pathology in APP/PS1 mice." *Nature* 493(7434): 674-678.

Holmes, C., D. Boche, D. Wilkinson, G. Yadegarfar, V. Hopkins, A. Bayer, R. W. Jones, R. Bullock, S. Love, J. W. Neal, E. Zotova and J. A. Nicoll (2008). "Long-term effects of Abeta42 immunisation in Alzheimer's disease: follow-up of a randomised, placebo-controlled phase I trial." *Lancet* 372(9634): 216-223.

Huang, Y. and L. Mucke (2012). "Alzheimer mechanisms and therapeutic strategies." *Cell* 148(6): 1204-1222.

Ikeda, S., C. W. Wong, D. Allsop, M. Landon, M. Kidd and G. G. Glenner (1987). "Immunogold labeling of cerebrovascular and neuritic plaque amyloid fibrils in Alzheimer's disease with an anti-beta protein monoclonal antibody." *Lab Invest* 57(4): 446-449.

Jiang, W., Y. Zhang, F. Meng, B. Lian, X. Chen, X. Yu, E. Dai, S. Wang, X. Liu, X. Li, L. Wang and X. Li (2013). "Identification of active transcription factor and miRNA regulatory pathways in Alzheimer's disease." *Bioinformatics* 29(20): 2596-2602.

Kitamura, Y., S. Shimohama, T. Ota, Y. Matsuoka, Y. Nomura and T. Taniguchi (1997). "Alteration of transcription factors NF-kappaB and STAT1 in Alzheimer's disease brains." *Neurosci Lett* 237(1): 17-20.

Morelli, L., M. I. Prat and E. M. Castano (1999). "Differential accumulation of soluble amyloid beta peptides 1-40 and 1-42 in human monocytic and neuroblastoma cell lines. Implications for cerebral amyloidogenesis." *Cell Tissue Res* 298(2): 225-232.

Ozudogru, S. N. and C. F. Lippa (2012). "Disease modifying drugs targeting beta-amyloid." *Am J Alzheimers Dis Other Demen* 27(5): 296-300.

Palop, J. J. and L. Mucke (2009). "Epilepsy and cognitive impairments in Alzheimer disease." *Arch Neurol* 66(4): 435-440.

Roher, A. E., M. O. Chaney, Y. M. Kuo, S. D. Webster, W. B. Stine, L. J. Haverkamp, A. S. Woods, R. J. Cotter, J. M. Tuohy, G. A. Krafft, B. S. Bonnell and M. R. Emmerling (1996). "Morphology and toxicity of Abeta-(1-42) dimer derived from neuritic and vascular amyloid deposits of Alzheimer's disease." *J Biol Chem* 271(34): 20631-20635.

Salloway, S., R. Sperling, N. C. Fox, K. Blennow, W. Klunk, M. Raskind, M. Sabbagh, L. S. Honig, A. P. Porsteinsson, S. Ferris, M. Reichert, N. Ketter, B. Nejadnik, V. Guenzler, M. Miloslavsky, D. Wang, Y. Lu, J. Lull, I. C. Tudor, E. Liu, M. Grundman, E. Yuen, R. Black, H. R. Brashear, Bapineuzumab and I. Clinical Trial (2014). "Two phase 3 trials of bapineuzumab in mild-to-moderate Alzheimer's disease." *N Engl J Med* 370(4): 322-333.

Schmidt, R., H. Schmidt, J. D. Curb, K. Masaki, L. R. White and L. J. Launer (2002). "Early inflammation and dementia: a 25-year follow-up of the Honolulu-Asia Aging Study." *Ann Neurol* 52(2): 168-174.

Selkoe, D. J. (2001). "Alzheimer's disease: genes, proteins, and therapy." *Physiol Rev* 81(2): 741-766.

Tabira, T. (2011). "[Immunotherapy targeting on Abeta for Alzheimer disease]." *Nihon Rinsho* 69 Suppl 10(Pt 2): 77-82.

Tai, D. J., W. L. Hsu, Y. C. Liu, Y. L. Ma and E. H. Lee (2011). "Novel role and mechanism of protein inhibitor of activated STAT1 in spatial learning." *EMBO J* 30(1): 205-220.

Tanzi, R. E. and L. Bertram (2005). "Twenty years of the Alzheimer's disease amyloid hypothesis: a genetic perspective." *Cell* 120(4): 545-555.

Weggen, S., J. L. Eriksen, P. Das, S. A. Sagi, R. Wang, C. U. Pietrzik, K. A. Findlay, T. E. Smith, M. P. Murphy, T. Bulter, D. E. Kang, N. Marquez-Sterling, T. E. Golde and E. H. Koo (2001). "A subset of NSAIDs lower amyloidogenic Abeta42 independently of cyclooxygenase activity." *Nature* 414(6860): 212-216.

Wisniewski, T. (2012). "Active immunotherapy for Alzheimer's disease." *Lancet Neurol* 11(7): 571-572.

Wolfe, M. S., J. De Los Angeles, D. D. Miller, W. Xia and D. J. Selkoe (1999). "Are presenilins intramembrane-cleaving proteases? Implications for the molecular mechanism of Alzheimer's disease." *Biochemistry* 38(35): 11223-11230.

We claim:

1. A method of treating Alzheimer's disease (AD) in a subject, the method comprising administering to the subject a pharmaceutically effective amount of a cholesterol 25-hydroxylase (CH25H inhibitor, wherein the CH25H inhibitor is a CRISPR-Cas9 or CRISPR-Cpf1 system targeting the CH25H gene.

2. The method of claim 1, wherein the CH25H inhibitor is a CRISPR-Cas9 system targeting the CH25H gene.

3. The method of claim 1, wherein the CH25H inhibitor is a CRISPR-Cpf1 system targeting the CH25H gene.

4. The method of claim 2, wherein the CRISPR-Cas9 system comprises a single guide RNA (sgRNA targeting the CH25H gene, wherein the sgRNA comprises the sequence as set forth in SEQ ID NO:1.

5. The method of claim 2, wherein the CRISPR-Cas9 system comprises a sgRNA targeting the CH25H gene, wherein the sgRNA comprises the sequence as set forth in SEQ ID NO:2.

6. (Presently Presented) The method of claim 2, wherein the CRISPR-Cas9 system produces targeted deletion of at least a part of the CH25H gene.

* * * * *

```
                        SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggcagaagct gctttacgga                                             20
```

```
<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gctgacactc taccagcacc                                              20
```